(12) United States Patent
Yu et al.

(10) Patent No.: US 10,724,101 B2
(45) Date of Patent: Jul. 28, 2020

(54) BIOMARKER SCNN1B FOR GASTRIC CANCER

(71) Applicant: The Chinese University of Hong Kong, Shatin (CN)

(72) Inventors: Jun Yu, Lake Silver (CN); Joseph Jao Yiu Sung, Ma On Shan (CN); Chi Chun Wong, Hong Kong (CN)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 66 days.

(21) Appl. No.: 15/074,323

(22) Filed: Mar. 18, 2016

(65) Prior Publication Data

US 2017/0268062 A1    Sep. 21, 2017

(51) Int. Cl.
 *C12Q 1/6886*    (2018.01)
 *G01N 33/574*    (2006.01)

(52) U.S. Cl.
 CPC ..... *C12Q 1/6886* (2013.01); *G01N 33/57446* (2013.01); *C12Q 2600/118* (2013.01); *C12Q 2600/154* (2013.01); *C12Q 2600/158* (2013.01)

(58) Field of Classification Search
 None
 See application file for complete search history.

(56) References Cited

U.S. PATENT DOCUMENTS

2014/0348749 A1* 11/2014 Birsoy ............... G01N 33/5011
                                                                424/9.2

FOREIGN PATENT DOCUMENTS

WO    WO 2008/013969    *    1/2008

OTHER PUBLICATIONS

Qian et al. Sodium channel subunit SCNN1B suppresses gastric cancer growth and metastasis via GRP78 degradation. Author Manuscript Published OnlineFirst on Feb. 15, 2017, pp. 1-27 and Figures 1-7.*
Guy, Bruno. Evaluation of Events Occurring at Mucosal Surfaces: Techniques used to collect and analyze mucosal secretions and cells. Clinical and Diagnostic Laboratory Immunology 9(4): 753-762, Jul. 2002.*
Dalgin et al., "Identification of Novel Epigenetic Markers for Clear Cell Renal Cell Carcinoma," *The Journal of Urology*, vol. 180, Sep. 2008, pp. 1126-1130.
Grady et al., "Genomic and Epigenetic Instability in Colorectal Cancer Pathogenesis," *Gastroenterology*, 2008; 135;1079-1099.
Rossier et al., "Epitheial Sodium Channel and the Control of Sodium Balance: Interaction Between Genetic and Environmental Factors," *Annu. Rev. Physiol.* 2002, 64:877-97.
Soundararajan et al., "Epithelial Sodium Channel Regulated by Differential Composition of a Signaling Complex," *PNAS*, May 12, 2009, vol. 106, No. 19, 7804-7809.
Yu et al., "Methylation of Protocadherin 10, a Novel Tumor Suppressor, is Associated with poor Prognosis in Patients with Gastric Cancer," *Gastroenterology*, 2009; 136: 640-651.

* cited by examiner

*Primary Examiner* — Alana Harris Dent
(74) *Attorney, Agent, or Firm* — Kilpatrick Townsend & Stockton LLP

(57) ABSTRACT

The present invention provides a method for diagnosing and determining prognosis of gastric cancer in a subject by detecting suppressed expression of the SCNN1B gene, which in some cases is due to elevated methylation level in the genomic sequence of this gene. A kit and device useful for such a method are also provided. In addition, the present invention provides a method for treating gastric cancer by increasing SCNN1B gene expression or activity.

13 Claims, 8 Drawing Sheets
Specification includes a Sequence Listing.

SEQUENCE LISTING

```
<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: synthetic primer sequence

<400> SEQUENCE: 1
agacaaccac aatggcttaa ca                                              22

<210> SEQ ID NO 2
<211> LENGTH: 22
<212> TYPE: DNA
<213> ORGANISM: Artificial Sequence
<220> FEATURE:
<223> OTHER INFORMATION: synthetic primer sequence

<400> SEQUENCE: 2
```
tgaggctaca tagtctcatg gc                                                    22

<210> SEQ ID NO 3
<211> LENGTH: 21
<212> TYPE: DNA
<213> ORGANISM: Artificial Sequence
<220> FEATURE:
<223> OTHER INFORMATION: synthetic primer sequence

<400> SEQUENCE: 3
gtttagtgtt tttgaatttg g                                                     21

<210> SEQ ID NO 4
<211> LENGTH: 24
<212> TYPE: DNA
<213> ORGANISM: Artificial Sequence
<220> FEATURE:
<223> OTHER INFORMATION: synthetic primer sequence

<400> SEQUENCE: 4
cttctacacc ctaaaaactt ttcc                                                  24

<210> SEQ ID NO 5
<211> LENGTH: 19
<212> TYPE: DNA
<213> ORGANISM: Artificial Sequence
<220> FEATURE:
<223> OTHER INFORMATION: synthetic primer sequence

<400> SEQUENCE: 5
gtgtggttag gtcggtagc                                                        19

<210> SEQ ID NO 6
<211> LENGTH: 19
<212> TYPE: DNA
<213> ORGANISM: Artificial Sequence
<220> FEATURE:
<223> OTHER INFORMATION: synthetic primer sequence

<400> SEQUENCE: 6
aacactaaaa cacccgacg                                                        19

<210> SEQ ID NO 7
<211> LENGTH: 19
<212> TYPE: DNA
<213> ORGANISM: Artificial Sequence
<220> FEATURE:
<223> OTHER INFORMATION: synthetic primer sequence

<400> SEQUENCE: 7
gtgtggttag gttggtagt                                                        19

<210> SEQ ID NO 8
<211> LENGTH: 19
<212> TYPE: DNA
<213> ORGANISM: Artificial Sequence
<220> FEATURE:
<223> OTHER INFORMATION: synthetic primer sequence

<400> SEQUENCE: 8
aacactaaaa cacccaaca                                                        19

<210> SEQ ID NO 9
<211> LENGTH: 532
<212> TYPE: DNA

<213> ORGANISM: Homo sapiens

<400> SEQUENCE: 9

| | | | | | |
|---|---|---|---|---|---|
| gtttagtgtt | tttgaatttg | gtgtgtgggg | gttggagttt | attgggaggt | gagggaggtg | 60 |
| gttaggggag | ttgggattgt | gtgtgtggtt | aggttggtag | tgtttagtaa | gttttatttg | 120 |
| tgggtgtttt | ttgtgttttt | ttgttttttga | atttgttttt | ttttagttgg | ttttgttgtg | 180 |
| tttgttgggt | gttttagtgt | tattaatatt | tggttgttgt | tgttagtttg | gtgtgtattg | 240 |
| ttgttttttgt | tattgttgat | agtgtgtatt | ttttgtgttt | ttgttttgtt | gtttgagtag | 300 |
| gtatgatggt | gaattttggt | ttgtatttgg | tttttttgtgt | gttgtttgga | gttttttgtgt | 360 |
| gtgtgttttt | ttttgtttaa | ttttggtttg | tgagttttttg | ttttggtttt | agttttttat | 420 |
| gggaggggtgt | ttgggtgttt | gtttgaggtg | tttgggattt | ggtttgggga | ttgaatgggt | 480 |
| tgggggtgga | ggggagagtt | ggaggttggg | aaaagttttt | agggtgtaga | ag | 532 |

<210> SEQ ID NO 10
<211> LENGTH: 1923
<212> TYPE: DNA
<213> ORGANISM: Homo sapiens

<400> SEQUENCE: 10

| | | | | | |
|---|---|---|---|---|---|
| atgcacgtga | agaagtacct | gctgaagggc | ctgcatcggc | tgcagaaggg | ccccggctac | 60 |
| acgtacaagg | agctgctggt | gtggtactgc | gacaacacca | cacccacgg | ccccaagcgc | 120 |
| atcatctgtg | aggggcccaa | gaagaaagcc | atgtggttcc | tgctcaccct | gctcttcgcc | 180 |
| gccctcgtct | gctggcagtg | gggcatcttc | atcaggacct | acttgagctg | ggaggtcagc | 240 |
| gtctccctct | ccgtaggctt | caagaccatg | gacttccctg | ccgtcaccat | ctgcaatgct | 300 |
| agccccttca | gtattccaa | atcaagcat | ttgctgaagg | acctggatga | gctgatggaa | 360 |
| gctgtcctgg | agagaatcct | ggctcctgag | ctaagccatg | ccaatgccac | caggaacctg | 420 |
| aacttctcca | tctggaacca | cacaccctg | gtccttattg | atgaacggaa | ccccaccac | 480 |
| cccatggtcc | ttgatctctt | tggagacaac | cacaatggct | aacaagcag | ctcagcatca | 540 |
| gaaaagatct | gtaatgccca | cgggtgcaaa | atggccatga | actatgtag | cctcaacagg | 600 |
| acccagtgta | ccttccggaa | cttcaccagt | gctacccagg | cattgacaga | gtggtacatc | 660 |
| ctgcaggcca | ccaacatctt | tgcacaggtg | ccacagcagg | agctagtaga | gatgagctac | 720 |
| cccggcgagc | agatgatcct | ggcctgccta | ttcggagctg | agccctgcaa | ctaccggaac | 780 |
| ttcacgtcca | tcttctaccc | tcactatggc | aactgttaca | tcttcaactg | ggcatgaca | 840 |
| gagaaggcac | ttccttcggc | caaccctgga | actgaattcg | gcctgaagtt | gatcctggac | 900 |
| ataggccagg | aagactacgt | cccccttcctt | gcgtccacgg | ccggggtcag | gctgatgctt | 960 |
| cacgagcaga | ggtcataccc | cttcatcaga | gatgagggca | tctacgccat | gtcggggaca | 1020 |
| gagacgtcca | tcggggtact | cgtggacaag | cttcagcgca | tggggagcc | ctacagcccg | 1080 |
| tgcaccgtga | atggttctga | ggtccccgtc | caaaacttct | acagtgacta | caacacgacc | 1140 |
| tactccatcc | aggcctgtct | tcgctcctgc | ttccaagacc | acatgatccg | taactgcaac | 1200 |
| tgtggccact | acctgtaccc | actgcccgt | ggggagaaat | actgcaacaa | ccggacttc | 1260 |
| ccagactggg | cccattgcta | ctcagatcta | cagatgagcg | tggcgcagag | agagacctgc | 1320 |
| attggcatgt | gcaaggagtc | ctgcaatgac | acccagtaca | agatgaccat | ctccatggct | 1380 |
| gactggcctt | ctgaggcctc | cgaggactgg | attttccacg | tcttgtctca | ggagcgggac | 1440 |
| caaagcacca | atatcacct | gagcaggaag | ggaattgtca | agctcaacat | ctacttccaa | 1500 |

```
gaatttaact atcgcaccat tgaagaatca gcagccaata acatcgtctg gctgctctcg    1560
aatctgggtg gccagtttgg cttctggatg gggggctctg tgctgtgcct catcgagttt    1620
ggggagatca tcatcgactt tgtgtggatc accatcatca agctggtggc cttggccaag    1680
agcctacggc agcggcgagc ccaagccagc tacgctggcc accgcccac cgtggccgag     1740 ctggtggagg cccacaccaa ctttggcttc cagcctgaca cggccccccg cagcccaac     1800 actgggccct accccagtga gcaggccctg cccatcccag caccccgcc cccaactat      1860 gactccctgc gtctgcagcc gctggacgtc atcgagtctg acagtgaggg tgatgccatc    1920
taa                                                                  1923

<210> SEQ ID NO 11
<211> LENGTH: 2597
<212> TYPE: DNA
<213> ORGANISM: Homo sapiens

<400> SEQUENCE: 11
gtgcttcccc gcccctgaac ctgctccctc ccagtcggtc tcgccgcgct cgccgggtgt      60
cccagtgtca ccaacactcg gccgccgccg ccagcttggc gcgcaccgcc gcctccgcca    120
ccgccgacag cgcgcatcct ccgtgtcccc gctccgccgc ccgagcaggt gccactatgc    180
acgtgaagaa gtacctgctg aagggcctgc atcggctgca aagggcccc ggctacacgt     240 acaaggagct gctggtgtgg tactgcgaca caccaacac ccacggcccc aagcgcatca     300
tctgtgaggg gcccaagaag aaagccatgt ggttcctgct caccctgctc ttcgccgccc    360
tcgtctgctg gcagtggggc atcttcatca ggacctactt gagctgggag gtcagcgtct    420
ccctctccgt aggcttcaag accatggact cccctgccgt caccatctgc aatgctagcc    480
ccttcaagta ttccaaaatc aagcatttgc tgaaggacct ggatgagctg atggaagctg    540
tcctggagag aatcctggct cctgagctaa gccatgccaa tgccaccagg aacctgaact    600
tctccatctg gaaccacaca cccctggtcc ttattgatga acggaacccc caccaccca     660 tggtccttga tctctttgga gacaaccaca atggcttaac aagcagctca gcatcagaaa    720
agatctgtaa tgcccacggg tgcaaaatgg ccatgagact atgtagcctc aacaggaccc    780
agtgtaccct tccggaactt caccagtgcta cccaggcatt gacagagtgg tacatcctgc    840
aggccaccaa catctttgca caggtgccac agcaggagct agtagagatg agctaccccg    900
gcgagcagat gatcctggcc tgcctattcg gagctgagcc ctgcaactac cggaacttca    960
cgtccatctt ctaccctcac tatggcaact gttacatctt caactggggc atgacagaga    1020
aggcacttcc ttcggccaac cctggaactg aattcggcct gaagttgatc ctggacatag    1080
gccaggaaga ctacgtcccc ttccttgcgt ccacggccgg ggtcaggctg atgcttcacg    1140
agcagaggtc atacccttc atcagagatg agggcatcta cgccatgtcg gggacagaga    1200
cgtccatcgg ggtactcgtg acaagcttc agcgcatggg ggagccctac agcccgtgca    1260
ccgtgaatgg ttctgaggtc cccgtccaaa acttctacag tgactacaac acgacctact    1320
ccatccaggc ctgtcttcgc tcctgcttcc aagaccacat gatccgtaac tgcaactgtg    1380
gccactacct gtacccactg ccccgtgggg agaaatactg caacaaccgg acttcccag    1440 actgggccca ttgctactca gatctacaga tgagcgtggc gcagagagag acctgcattg    1500
gcatgtgcaa ggagtcctgc aatgacaccc agtacaagat gaccatctcc atggctgact    1560
ggccttctga ggcctccgag gactggattt ccacgtctct tgtctcagga gcggaccaaa    1620
```

```
gcaccaatat cacccthgagc aggaagggaa ttgtcaagct caacatctac ttccaagaat    1680
ttaactatcg caccattgaa gaatcagcag ccaataacat cgtctggctg ctctcgaatc    1740
tgggtggcca gtttggcttc tggatggggg gctctgtgct gtgcctcatc gagtttgggg    1800
agatcatcat cgactttgtg tggatcacca tcatcaagct ggtggccttg ccaagagcc     1860 tacggcagcg gcgagcccaa gccagctacg ctggcccacc gcccaccgtg gccgagctgg    1920
tggaggccca caccaacttt ggcttccagc ctgacacggc ccccgcagc cccaacactg     1980 ggccctaccc cagtgagcag gccctgccca tcccaggcac cccgccccc aactatgact     2040 ccctgcgtct gcagccgctg gacgtcatcg agtctgacag tgagggtgat gccatctaac    2100 cctgccctg cccaccccgg gcggctgaaa ctcactgagc agccaagact gttgcccgag     2160
gcctcactgt atggtgccct ctccaaaggg tcgggagggt agctctccag gccagagctt    2220
gtgtccttca acagagaggc cagcggcaac tggtccgtta ctggccaagg gctctgtaga    2280
atcacggtgc tggtacagga tgcaggaata aattgtatct tcacctggtt cctaccctcg    2340
tccctacctg tcctgatcct ggtcctgaag acccctcgga cacccctctc ctggtggcag    2400
gccacttccc tcccagtgcc agtctccatc caccccagag aggaacaggc gggtgggcca    2460
tgtggttttc tccttcctgg ccttggctgg cctctggggc aggggtggtg gagagatgga    2520
agggcatcag gtgtagggac cctgccaagt ggcacctgat ttactctaga aaataaaagt    2580
agaaaatact gagtcca                                                   2597
```

<210> SEQ ID NO 12
<211> LENGTH: 640
<212> TYPE: PRT
<213> ORGANISM: Homo sapiens

<400> SEQUENCE: 12

```
Met His Val Lys Lys Tyr Leu Leu Lys Gly Leu His Arg Leu Gln Lys
1               5                   10                  15

Gly Pro Gly Tyr Thr Tyr Lys Glu Leu Leu Val Trp Tyr Cys Asp Asn
            20                  25                  30

Thr Asn Thr His Gly Pro Lys Arg Ile Ile Cys Glu Gly Pro Lys Lys
        35                  40                  45

Lys Ala Met Trp Phe Leu Leu Thr Leu Leu Phe Ala Ala Leu Val Cys
    50                  55                  60

Trp Gln Trp Gly Ile Phe Ile Arg Thr Tyr Leu Ser Trp Glu Val Ser
65                  70                  75                  80

Val Ser Leu Ser Val Gly Phe Lys Thr Met Asp Phe Pro Ala Val Thr
                85                  90                  95

Ile Cys Asn Ala Ser Pro Phe Lys Tyr Ser Lys Ile Lys His Leu Leu
            100                 105                 110

Lys Asp Leu Asp Glu Leu Met Glu Ala Val Leu Glu Arg Ile Leu Ala
        115                 120                 125

Pro Glu Leu Ser His Ala Asn Ala Thr Arg Asn Leu Asn Phe Ser Ile
    130                 135                 140

Trp Asn His Thr Pro Leu Val Leu Ile Asp Glu Arg Asn Pro His His
145                 150                 155                 160

Pro Met Val Leu Asp Leu Phe Gly Asp Asn His Asn Gly Leu Thr Ser
                165                 170                 175

Ser Ser Ala Ser Glu Lys Ile Cys Asn Ala His Gly Cys Lys Met Ala
            180                 185                 190

Met Arg Leu Cys Ser Leu Asn Arg Thr Gln Cys Thr Phe Arg Asn Phe
```

```
            195                 200                 205
Thr Ser Ala Thr Gln Ala Leu Thr Glu Trp Tyr Ile Leu Gln Ala Thr
210                 215                 220
Asn Ile Phe Ala Gln Val Pro Gln Gln Glu Leu Val Glu Met Ser Tyr
225                 230                 235                 240
Pro Gly Glu Gln Met Ile Leu Ala Cys Leu Phe Gly Ala Glu Pro Cys
                    245                 250                 255
Asn Tyr Arg Asn Phe Thr Ser Ile Phe Tyr Pro His Tyr Gly Asn Cys
                260                 265                 270
Tyr Ile Phe Asn Trp Gly Met Thr Glu Lys Ala Leu Pro Ser Ala Asn
            275                 280                 285
Pro Gly Thr Glu Phe Gly Leu Lys Leu Ile Leu Asp Ile Gly Gln Glu
290                 295                 300
Asp Tyr Val Pro Phe Leu Ala Ser Thr Ala Gly Val Arg Leu Met Leu
305                 310                 315                 320
His Glu Gln Arg Ser Tyr Pro Phe Ile Arg Asp Glu Gly Ile Tyr Ala
                    325                 330                 335
Met Ser Gly Thr Glu Thr Ser Ile Gly Val Leu Val Asp Lys Leu Gln
                340                 345                 350
Arg Met Gly Glu Pro Tyr Ser Pro Cys Thr Val Asn Gly Ser Glu Val
            355                 360                 365
Pro Val Gln Asn Phe Tyr Ser Asp Tyr Asn Thr Thr Tyr Ser Ile Gln
370                 375                 380
Ala Cys Leu Arg Ser Cys Phe Gln Asp His Met Ile Arg Asn Cys Asn
385                 390                 395                 400
Cys Gly His Tyr Leu Tyr Pro Leu Pro Arg Gly Glu Lys Tyr Cys Asn
                    405                 410                 415
Asn Arg Asp Phe Pro Asp Trp Ala His Cys Tyr Ser Asp Leu Gln Met
                420                 425                 430
Ser Val Ala Gln Arg Glu Thr Cys Ile Gly Met Cys Lys Glu Ser Cys
            435                 440                 445
Asn Asp Thr Gln Tyr Lys Met Thr Ile Ser Met Ala Asp Trp Pro Ser
450                 455                 460
Glu Ala Ser Glu Asp Trp Ile Phe His Val Leu Ser Gln Glu Arg Asp
465                 470                 475                 480
Gln Ser Thr Asn Ile Thr Leu Ser Arg Lys Gly Ile Val Lys Leu Asn
                    485                 490                 495
Ile Tyr Phe Gln Glu Phe Asn Tyr Arg Thr Ile Glu Glu Ser Ala Ala
                500                 505                 510
Asn Asn Ile Val Trp Leu Leu Ser Asn Leu Gly Gly Gln Phe Gly Phe
            515                 520                 525
Trp Met Gly Gly Ser Val Leu Cys Leu Ile Glu Phe Gly Glu Ile Ile
530                 535                 540
Ile Asp Phe Val Trp Ile Thr Ile Ile Lys Leu Val Ala Leu Ala Lys
545                 550                 555                 560
Ser Leu Arg Gln Arg Arg Ala Gln Ala Ser Tyr Ala Gly Pro Pro Pro
                    565                 570                 575
Thr Val Ala Glu Leu Val Glu Ala His Thr Asn Phe Gly Phe Gln Pro
                580                 585                 590
Asp Thr Ala Pro Arg Ser Pro Asn Thr Gly Pro Tyr Pro Ser Glu Gln
            595                 600                 605
Ala Leu Pro Ile Pro Gly Thr Pro Pro Asn Tyr Asp Ser Leu Arg
610                 615                 620
```

```
Leu Gln Pro Leu Asp Val Ile Glu Ser Asp Ser Glu Gly Asp Ala Ile
625                 630                 635                 640

<210> SEQ ID NO 13
<211> LENGTH: 294
<212> TYPE: DNA
<213> ORGANISM: Artificial Sequence
<220> FEATURE:
<223> OTHER INFORMATION: synthetic nucleotide sequence with CpG sites

<400> SEQUENCE: 13
ggcgtgtggg ggctggagct tattgggagg cgagggaggt ggccagggga gccgggaccg     60
tgcgtgtggc caggccggta gcgcccagta agctccaccc gcgggcgctc cccgtgcttc    120
cccgcccctg aacctgctcc ctcccagtcg gtctcgccgc gctcgccggg tgtcccagtg    180
tcaccaacac tcggccgccg ccgccagctt ggcgcgcacc gccgcctccg ccaccgccga    240
cagcgcgcat cctccgtgtc cccgctccgc cgcccgagca ggtatgacgg cgaa          294
```

BIOMARKER SCNN1B FOR GASTRIC CANCER

BACKGROUND OF THE INVENTION

Gastric cancer, also known as stomach cancer, is the fourth most common cancer worldwide with approximately 1,000,000 cases diagnosed annually. It is a disease with a high mortality rate (about 800,000 deaths per year), making it the second most common cause of cancer death worldwide after lung cancer. The incidence of gastric cancer is significantly higher among men and in developing nations, including many Asian countries.

Gastric cancer often remains asymptomatic or exhibits only nonspecific symptoms in its early stages, diagnosis in many cases is therefore not made until the disease has reached an advanced stage. This leads to a generally poor prognosis: metastasis occurs in 80-90% of individuals diagnosed with gastric cancer, with a six-month survival rate of 65% in those diagnosed in early stages and less than 15% of those diagnosed in late stages.

Because of the prevalence of gastric cancer and its grave implications on patients' life expectancy, there exists an urgent need for new and more effective methods to diagnose, monitor, and treat gastric cancer. This invention fulfills this and other related needs.

BRIEF SUMMARY OF THE INVENTION

The present inventors have identified SCNN1B as a novel tumor suppressor and diagnostic/prognostic marker for human gastric cancer. More specifically, the inventors show that, compared with normal individuals, CpG islands of SCNN1B gene are hypermethylated in biological samples of cancer tissues from gastric cancer patients. Such hypermethylation leads to SCNN1B silencing at both mRNA and protein levels. Re-expression of SCNN1B inhibits cancer cell growth and induces programmed cell death. Protein/mRNA expression level of SCNN1B and promoter methylation level of SCNN1B genetic sequence closely correlate with the survival of gastric cancer patients and are therefore also useful as prognostic markers for gastric cancer.

As such, in the first aspect, the present invention provides a method for assessing the risk for gastric cancer in a subject, i.e., the likelihood of gastric cancer being present in the subject and/or the likelihood of the subject developing the disease at a later time. The method includes the steps of: (a) measuring expression level of SCNN1B in a sample taken from the subject, and (b) comparing the expression level obtained in step (a) with a standard control. When a decrease in the expression level of SCNN1B is detected as compared with the standard control, it indicates that the subject may have gastric cancer or have an increased risk for gastric cancer. Typically, the sample used in the method is a stomach mucosa sample, e.g., one that includes stomach epithelial cells. The subject being tested may be a human or a member of other mammals such as primates, who may or may not exhibit any signs indicative of any condition or abnormality relating to the stomach.

In some embodiments, the expression level of SCNN1B is the SCNN1B protein level. In other embodiments, the expression level of SCNN1B is SCNN1B mRNA level. When the SCNN1B protein level is measured, step (a) may include an immunoassay using an antibody that specifically binds the SCNN1B protein. For example, a Western Blot analysis may be used. In other cases, step (a) may involve mass spectrometry, or a hybridization-based assay such as hybridization to a microarray, fluorescence probe, or molecular beacon.

When SCNN1B mRNA level is measured, step (a) in some cases may involve an amplification reaction, such as a polymerase chain reaction (PCR), especially a reverse transcriptase-PCR (RT-PCR). In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:10 or 11 or a complement thereof. In some cases, the polynucleotide probe may include a detectable moiety.

In some embodiments, when the subject is indicated as having gastric cancer or having an increased risk of gastric cancer after the first round of method steps described above, the claimed method may further include repeating the same steps at a later time using the same type of sample from the subject. An increase in the expression level of SCNN1B at the later time as compared to the amount from the original step (a) indicates an improvement of gastric cancer or a lessened risk for the disease, whereas a decrease indicates a worsening of gastric cancer or a heightened risk for the disease.

In a second aspect, the present invention provides another method for detecting gastric cancer or assessing risk of gastric cancer in a subject. The method includes the steps of: (a) treating a sample taken from the subject with an agent that differentially modifies methylated and unmethylated DNA; and (b) determining whether each CpG in a CpG-containing genomic sequence is methylated or unmethylated, thus determining the number of methylated CpGs within this sequence, with the CpG-containing genomic sequence being at least a segment of SEQ ID NO:9 and comprising at least 1, 2, 3, 4, 5, 6, 7, 8, 9, or 10 or more CpG pairs. When the presence of at least one, or at least 5 or 10 methylated CpGs (for example, at least 50% of total CpGs), is detected in the CpG-containing genomic sequence, it indicates that the subject may have gastric cancer or is at an increased risk of developing the disease. In some cases, the number of methylated CpGs is compared with a control number, e.g., the number of methylated CpGs in the same genomic sequence determined following the same process described above using a sample of the same type from non-cancerous tissue originated from a healthy control subject who has been determined as having no gastric cancer or no known risk for the disease. When the number of methylated CpGs is higher in the test subject compared to the control number, the test subject is determined as having gastric cancer or having an increased risk for the disease; otherwise the test subject is determined as not having gastric cancer or not having any elevated risk for developing the disease.

In some embodiments, the CpG-containing genomic sequence contains two or more CpGs, and when at least 50% of all CpG being methylated the subject is indicated as having or at an increased risk for gastric cancer. In some cases, the CpG-containing genomic sequence is a segment of at least 15, 20, 50, 100, 125, 150, 200, 250, or more contiguous nucleotides of SEQ ID NO:9, for example, segment 53-174 of SEQ ID NO:9. In other cases, the CpG-containing genomic sequence is SEQ ID NO:9. In one embodiment of the claimed method, the CpG-containing genomic sequence is SEQ ID NO:9, and when at least 10 of all CpG in the CpG-containing genomic sequence are methylated, the subject is indicated as having gastric cancer or having an increased risk for gastric cancer.

In some examples, the sample used in the claimed method is a stomach mucosa sample. In other examples, when the subject is indicated as having gastric cancer after the first round of method steps described above, the method further involves repeating steps (a) and (b) at a later time using the sample type of sample from the subject. When an increase is detected in the number of methylated CpG at the later time as compared to the number of methylated CpG determined from the original step (b), it indicates a worsening of gastric cancer, whereas a decrease indicates an improvement of gastric cancer.

In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite (e.g., sodium bisulfite). In other embodiments, step (b) of the method involves an amplification reaction; or step (b) may involve sequencing of a DNA molecule.

In a third aspect, the present invention provides a method for assessing likelihood of mortality in a gastric cancer patient. The method includes the steps of: (a) treating a sample taken from a gastric cancer patient, who has received a diagnosis of gastric cancer, with an agent that differentially modifies methylated and unmethylated DNA; and (b) determining whether each CpG in a CpG-containing genomic sequence is methylated or unmethylated, thus determining the number of methylated CpGs within this sequence, with the CpG-containing genomic sequence being at least a segment of SEQ ID NO:9 and comprising at least 1, 2, 3, 4, 5, 6, 7, 8, 9, or 10 or more CpG pairs. When the presence of at least 1 or 2, or at least 5 or 10 methylated CpGs (for example, at least 50% of total CpGs), is detected in the CpG-containing genomic sequence, it indicates that the subject has a high likelihood of mortality (e.g., more likely than not, or greater than 10%, 20%, 30%, 40%, 50%, 60%, 70%, 80%, or 90% chance of mortality) in a subsequent time period, e.g., 1, 2, 3, 4, or 5 years or up to 10 years. In some cases, the likelihood of mortality is compared between two subjects who both have received a diagnosis of gastric cancer. The number of methylated CpGs determined from the first patient's sample after steps (a) and (b) is then compared with the number of methylated CpGs in the same genomic sequence determined following the same process using a sample of the same type originated from the second patient. When the number of methylated CpGs is higher in the first patient's sample compared to the number in the second patient's sample, the first patient is determined as having a higher likelihood of mortality due to gastric cancer than the second patient in a subsequent time period, e.g., 1, 2, 3, 4, or 5 years or up to 10 years. In some cases, the comparison is made between one test patient and an established low mortality patient who has been previously determined to have no or a very low number (e.g., 1 or 2) of methylated CpGs in the genomic sequence. When the test subject is found to have more methylated CpGs than the low mortality patient in the same genomic region, after both patients' samples have been processed through the method steps describe above, the test patient is deemed to have a higher likelihood of mortality due to gastric cancer than the low mortality patient for a subsequent time period of, e.g., 1, 2, 3, 4, or 5 years or up to 10 years.

In some embodiments, the CpG-containing genomic sequence analyzed in this method contains two or more CpGs. In some cases, the CpG-containing genomic sequence is a segment of at least 15, 20, 50, 100, 125, 150, 200, 250, or more contiguous nucleotides of SEQ ID NO:9. One such example is segment 53-174 of SEQ ID NO:9. In other cases, the CpG-containing genomic sequence is SEQ ID NO:9.

In some examples, the sample used in the claimed method is a stomach mucosa sample. In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite (e.g., sodium bisulfite). In other embodiments, step (b) of the method involves an amplification reaction such as a PCR; or step (b) may involve sequencing of a DNA molecule. In some embodiments, the PCR is performed using at least one primer consisting of the sequence set forth in SEQ ID NO:1, 2, 3, 4, 5, 6, 7, or 8, in combination with one or more other primer(s) appropriate for the amplification reaction.

In a related application of this invention, likelihood of mortality in a gastric cancer patient due to the disease can also be assessed by comparing the expression level of SCNN1B mRNA or protein among patients who have been diagnosed with gastric cancer. Briefly, the method for assessing likelihood of mortality includes the steps of: (a) measuring expression level of SCNN1B in a sample taken from a first patient who has been diagnosed with gastric cancer, and (b) comparing the expression level obtained in step (a) with the expression level of SCNN1B determined in a sample of same type that was taken from a second gastric cancer patient and measured in the same step (a). When the expression level of SCNN1B is higher in the first patient's sample than that found in the second patient's sample, the first patient is deemed as having a higher likelihood of mortality from gastric cancer than the second patient. Typically, the sample used in the method is a stomach mucosa sample, e.g., one that includes stomach epithelial cells. The subject being tested may be a human or a member of other mammals such as primates. In some cases, the second patient is one who has been diagnosed with gastric cancer but has been previously determined as having a normal expression level of SCNN1B mRNA and/or protein in the gastric cancer tissue.

In some embodiments of this method, the expression level of SCNN1B is the SCNN1B protein level. In other embodiments, the expression level of SCNN1B is SCNN1B mRNA level. When the SCNN1B protein level is measured, step (a) may include an immunoassay using an antibody that specifically binds the SCNN1B protein. For example, a Western Blot analysis may be used. In other cases, step (a) may involve mass spectrometry, or a hybridization-based assay such as hybridization to a microarray, fluorescence probe, or molecular beacon.

When SCNN1B mRNA level is measured, step (a) in some cases may involve an amplification reaction, such as a PCR, especially an RT-PCR. In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with at least a segment of SEQ ID NO:10 or 11 or a complement thereof. In some cases, the polynucleotide probe may include a detectable moiety. The sample used in this method is a stomach mucosa sample taken from confirmed cancerous tissues.

In a fourth aspect, the present invention provides a kit for detecting gastric cancer in a subject, comprising (1) a standard control that provides an average amount of SCNN1B protein or SCNN1B mRNA; and (2) an agent that specifically and quantitatively identifies SCNN1B protein or SCNN1B mRNA. In some cases, the agent may be an antibody that specifically binds the SCNN1B protein; or the agent may be a polynucleotide probe that hybridizes with the SCNN1B mRNA. For example, the polynucleotide probe hybridizes with at least a segment of SEQ ID NO:10 or 11 or a complement thereof. The agent may include a detectable moiety. In other cases, the kit may further comprise two oligonucleotide primers for specifically amplifying at least a segment of SEQ ID NO:10 or 11 or its complement in an amplification reaction. Typically, the kit will further include an instruction manual.

In a fifth aspect, the present invention provides a method for inhibiting growth of a gastric cancer cell. The claimed method includes the step of contacting the gastric cancer cell with (1) an effective amount of a polypeptide that comprises the amino acid sequence set forth in SEQ ID NO:12 or (2) a nucleic acid that comprises a polynucleotide sequence encoding SEQ ID NO:12. In some embodiments, the nucleic acid is an expression cassette comprising a promoter operably linked to the polynucleotide sequence encoding SEQ ID NO:12. Various promoters may be useful in this method, for example, the promoter may be an epithelium-specific promoter. In other embodiments, the nucleic acid comprises the polynucleotide sequence set forth in SEQ ID NO:10 or 11. In yet other embodiments, the gastric cancer cell is within a patient's body.

In addition, the present invention provides a kit for detecting gastric cancer. The kit comprises: (1) an agent that differentially modifies methylated and unmethylated DNA, and (2) an indicator that, after the agent has been used to treat a sample from a subject who is being tested for gastric cancer, determines whether each CpG in a CpG-containing genomic sequence is methylated or unmethylated. The CpG-containing genomic sequence is at least a segment of SEQ ID NO:9 and comprises at least 1, 2, 3, 4, 5, 6, 7, 8, 9, or 10 or more CpG pairs. The present invention also provides a composition for inhibiting growth of a gastric cancer cell. The composition contains an effective amount of (1) a polypeptide comprising the amino acid sequence set forth in SEQ ID NO:12 (e.g., a polypeptide consisting of the amino acid sequence of SEQ ID NO:12) or (2) a nucleic acid comprising or consisting of a polynucleotide sequence encoding SEQ ID NO:12 (e.g., a nucleic acid sequence comprising the polynucleotide sequence of SEQ ID NO:10 or 11), and a pharmaceutically acceptable carrier. In this regard, this invention further provides the use of a polypeptide comprising the amino acid sequence set forth in SEQ ID NO:12 (e.g., a polypeptide consisting of the amino acid sequence of SEQ ID NO:12) or a nucleic acid comprising a polynucleotide sequence encoding SEQ ID NO:10 or 11 (e.g., a nucleic acid sequence comprising or consisting of the polynucleotide sequence of SEQ ID NO:10 or 11) in preparing a medicament for inhibiting growth of a gastric cancer cell.

DEFINITIONS

Figure 1:
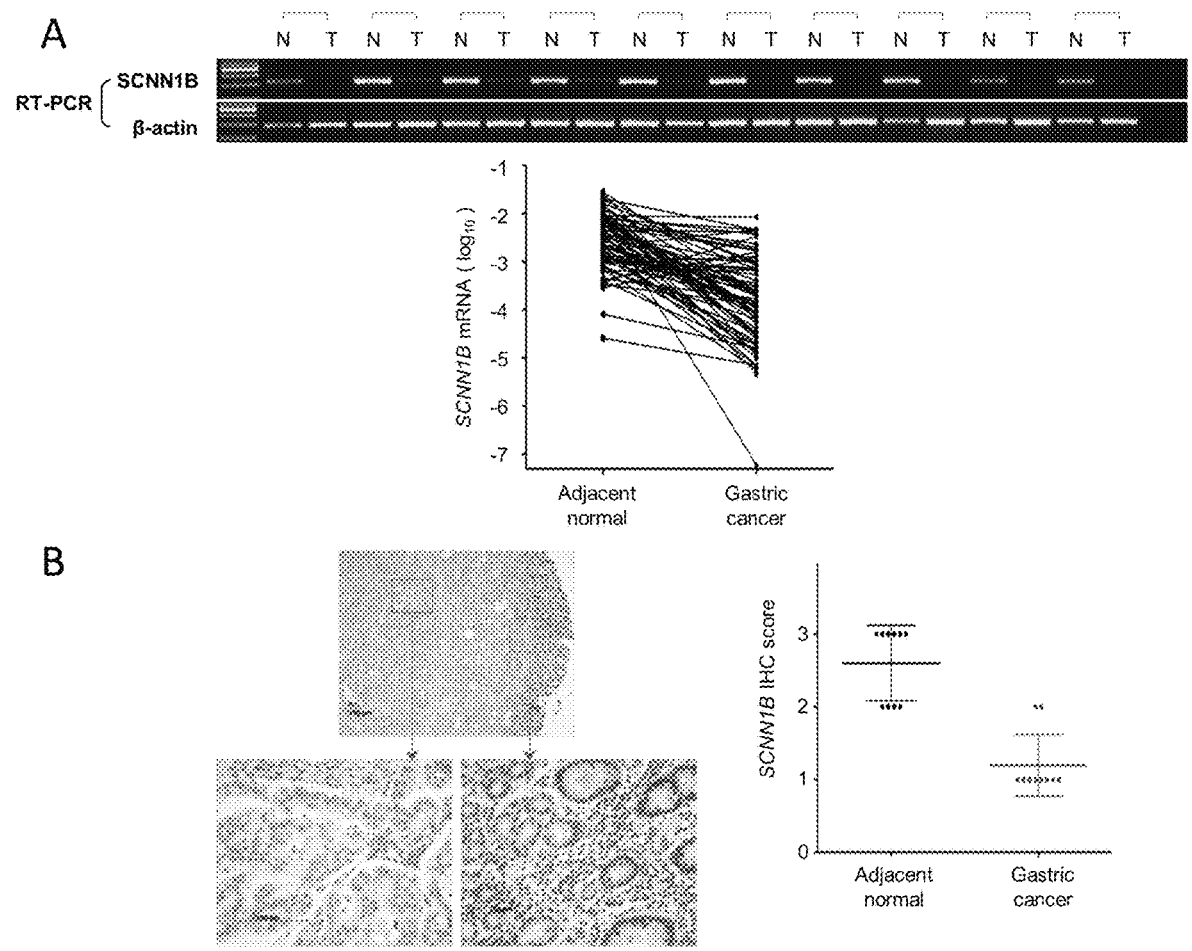
FIG. 1 shows promoter hypermethylation of SCNN1B led to down-regulation of SCNN1B in gastric cancer tissues in an embodiment.

The term "SCNN1B gene" or "SCNN1B protein," as used herein, refers to any naturally occurring variants or mutants, interspecies homologs or orthologs, or man-made variants of human SCNN1B gene or SCNN1B protein. The DNA sequence for a human wild-type SCNN1B mRNA is set forth in GenBank Accession No. NM_000336.2 (provided herein as SEQ ID NO:11), which translate to a coding sequence (provided herein as SEQ ID NO:10) for a 640-amino acid SCNN1B protein (provided herein as SEQ ID NO:12). A SCNN1B protein within the meaning of this application typically has at least 80%, or 90%, or 95% or higher sequence identity to the human wild-type SCNN1B protein.

In this disclosure the terms "gastric cancer" and "stomach cancer" have the same meaning and refer to a cancer of the stomach or of stomach cells. Such cancers may be adenocarcinomas that occur in the lining of the stomach (mucosa or stomach epithelium) and may be in pylorus, body, or cardial (lower, body and upper) parts of the stomach. A "gastric cancer cell" is a stomach epithelial cell possessing characteristics of gastric cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human SCNN1B protein) or the translation of a protein encoded by a polynucleotide sequence. In other words, both mRNA level and protein level encoded by a gene of interest (e.g., human SCNN1B gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant SCNN1B protein used in the method of this invention (e.g., for treating gastric cancer) has at least 80% sequence identity, preferably 85%, 90%, 91%, 92%, 93, 94%, 95%, 96%, 97%, 98%, 99%, or 100% identity, to a reference sequence, e.g., a wild-type human SCNN1B protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=–2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 200, 250, or 300 contiguous nucleotides in length and contains at least 2, 3, 4, 5, 6, 7, 8, 9, 10, 15, 20, 25, or 30 CpG pairs. For any one "CpG-containing genomic sequence" at a given location, e.g., within a region of the human SCNN1B genomic sequence (such as the region containing the promoter and exon 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of SCNN1B mRNA or SCNN1B protein found in non-cancerous stomach tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human SCNN1B or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., SCNN1B mRNA or SCNN1B protein, that is present in an established normal disease-free tissue sample, e.g., a normal stomach epithelial tissue sample. The standard control value is suitable for the use of a method of the present invention, to serve as a basis for comparing the amount of SCNN1B mRNA or SCNN1B protein that is present in a test sample. An established sample serving as a standard control provides an average amount of SCNN1B mRNA or SCNN1B protein that is typical for a stomach epithelial tissue sample (e.g., stomach mucosa) of an average, healthy human without any stomach disease especially gastric cancer as conventionally defined. A standard control value may vary depending on the nature of the sample as well as other factors such as the gender, age, ethnicity of the subjects based on whom such a control value is established.

The term "average," as used in the context of describing a human who is healthy, free of any stomach disease (especially gastric cancer) as conventionally defined, refers to certain characteristics, especially the amount of human SCNN1B mRNA or SCNN1B protein, found in the person's stomach tissue, e.g., epithelial tissue or gastric mucosa, that are representative of a randomly selected group of healthy humans who are free of any stomach diseases (especially gastric cancer). This selected group should comprise a sufficient number of humans such that the average amount of SCNN1B mRNA or protein in the stomach mucosa among these individuals reflects, with reasonable accuracy, the corresponding amount of SCNN1B mRNA/protein in the general population of healthy humans. In addition, the selected group of humans generally have a similar age to that of a subject whose stomach tissue sample is tested for indication of gastric cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human SCNN1B mRNA or SCNN1B protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding SCNN1B mRNA is the amount of said polynucleotide to achieve an increased level of SCNN1B protein expression or biological activity, such that the symptoms of gastric cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, gastric cancer. Subjects also include individuals currently undergoing therapy that seek manipulation of the therapeutic regimen. Subjects or individuals in need of treatment include those that demonstrate symptoms of gastric cancer or are at risk of suffering from gastric cancer or its symptoms. For example, a subject in need of treatment includes individuals with a genetic predisposition or family history for gastric cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of SCNN1B protein are used to refer to inhibitory, activating, or modulating molecules, respectively, identified using in vitro and in vivo assays for SCNN1B protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of SCNN1B protein. In some cases, the inhibitor directly or indirectly binds to SCNN1B protein, such as a neutralizing antibody. Inhibitors, as used herein, are synonymous with inactivators and antagonists. Activators are agents that, e.g., stimulate, increase, facilitate, enhance activation, sensitize or up regulate the activity of SCNN1B protein. Modulators include SCNN1B protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction

Gastric cancer patients often face a grim prognosis due to the nature of this disease in its lacking of specific symptoms during its early development stages. Early detection of gastric cancer is therefore critical for improving patient survival rate. Moreover, it is also of practical importance to predict the likelihood of mortality from gastric cancer among patients who have already received a diagnosis of gastric cancer for any time period after the diagnosis.

The present inventors discovered for the first time that expression of SCNN1B, both at the mRNA and protein levels, is suppressed in gastric cancer cells. This suppressed expression of SCNN1B protein is due to increased methylation in the SCNN1B genomic sequence, especially in the promoter region of the gene, which leads to decreased transcription of SCNN1B mRNA. This discovery provides important means for detecting, monitoring, and treating gastric cancer. Generally, a lower than normal SCNN1B mRNA/protein level seen in a test subject, who may or may not exhibit any signs of stomach-related disorder or condition, indicates a high likelihood that the subject already has or will later develop gastric cancer. Similarly, a higher than normal level of methylation in the SCCN1B gene sequence, especially in the promoter region, indicates a high likelihood that the subject already has or will later develop gastric cancer. Further, among gastric cancer patients, individuals with lower level of SCNN1B expression in mRNA or protein or higher level of SCNN1B DNA methylation suffer a higher likelihood of mortality from gastric cancer during a post-diagnosis time period in comparison with their counterparts who have a normal or higher level of SCNN1B expression in mRNA or protein or a normal or lower level of SCNN1B DNA methylation.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human SCNN1B gene, and synthetic oligonucleotides (e.g., primers) can be verified using, e.g., the chain termination method for sequencing double-stranded templates of Wallace et al., *Gene* 16: 21-26 (1981).

III. Acquisition of Tissue Samples and Analysis of SCNN1B mRNA or DNA

The present invention relates to measuring the amount of SCNN1B mRNA or analyzing the methylation pattern of SCNN1B genomic DNA found in a person's stomach tissue, especially stomach epithelial sample, as a means to detect the presence, to assess the risk of developing, and/or to monitor the progression or treatment efficacy of gastric cancer. Thus, the first steps of practicing this invention are to obtain a stomach epithelial tissue sample from a test subject and extract mRNA or DNA from the sample.

A. Acquisition and Preparation of Stomach Tissue Samples

A stomach tissue sample is obtained from a person to be tested or monitored for gastric cancer using a method of the present invention. Collection of stomach epithelial tissue sample from an individual is performed in accordance with the standard protocol hospitals or clinics generally follow, such as during an endoscopy. An appropriate amount of stomach epithelium is collected and may be stored according to standard procedures prior to further preparation.

The analysis of SCNN1B mRNA or DNA found in a patient's stomach epithelial sample according to the present invention may be performed using, e.g., stomach mucosa. The methods for preparing tissue samples for nucleic acid extraction are well known among those of skill in the art. For example, a subject's stomach mucosa sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human SCNN1B mRNA may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human SCNN1B mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The SCNN1B mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to SCNN1B mRNA can be used to detect the presence of such mRNA species and indicate the amount of mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

C. Detection of Methylation in SCNN1B Genomic Sequence

Methylation status of a segment of SCNN1B genomic sequence containing one or more CpG (cytosine-guanine dinucleotide) pairs is investigated to provide indication as to whether a test subject is suffering from gastric cancer, whether the subject is at risk of developing gastric cancer, or whether the subject's gastric cancer is worsening or improving.

Typically a segment of the SCNN1B genomic sequence that includes the 5' untranslated region (such as the promoter region) and includes one or more CpG nucleotide pairs is analyzed for methylation pattern. For example, SEQ ID NO:9 or a portion thereof can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of gastric cancer cells. The length of the sequence being analyzed is usually at least 15 or 20 contiguous nucleotides, and may be longer with at least 25, 30, 50, 100, 200, 300, 400, or more contiguous nucleotides. At least one, typically 2 or more, often 3, 4, 5, 6, 7, 8, 9, or more, CpG nucleotide pairs are present within the sequence. In the cases of multiple (2 or more) CpG sites are analyzed for methylation status, when at least 50% of the CpG pairs within the analyzed genomic sequence are shown to be methylated, subject being tested is deemed to have gastric cancer or have an elevated risk of developing gastric cancer. For example, SEQ ID NO:9, a segment of SCNN1B genomic sequence (−132 to +400 in relation to the transcription start site), and the 53-174 segment of SEQ ID NO:9 (the 121 bp MSP region in FIG. 3; SEQ ID NO:13) are such CpG-containing genomic sequences useful for the analysis. Some or majority of the CpG pairs in this region are found to be methylated in established gastric cancer cell lines and samples taken from gastric cancer, whereas non-cancerous stomach epithelial cells showed very few, if any at all, methylated CpG sites. For the purpose of determining the methylation pattern of a SCNN1B genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfate conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MS-PCR), methylation-sensitive single nucleotide primer extension (Ms-SnuPE), high resolution melting (HRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI.

2. Optional Amplification and Sequence Analysis

Following the modification of DNA in a methylation-differential manner, the treated DNA is then subjected to sequence-based analysis, such that the methylation status of the SCNN1B genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of stomach epithelium from a subject being tested, assessed, or monitored for gastric cancer, the risk of developing gastric cancer, or the severity/progression of the condition. Samples of the same type should be taken from both a control group (normal individuals not suffering from any stomach disorder especially neoplasia) and a test group (subjects being tested for possible gastric cancer, for example). Standard procedures routinely employed in hospitals or clinics are typically followed for this purpose, as stated in the previous section.

For the purpose of detecting the presence of gastric cancer or assessing the risk of developing gastric cancer in test subjects, individual patients' stomach mucosa samples may be taken and the level of human SCNN1B protein may be measured and then compared to a standard control. If a decrease in the level of human SCNN1B protein is observed when compared to the control level, the test subject is deemed to have gastric cancer or have an elevated risk of developing the condition. For the purpose of monitoring disease progression or assessing therapeutic effectiveness in gastric cancer patients, individual patient's stomach epithelial samples may be taken at different time points, such that the level of human SCNN1B protein can be measured to provide information indicating the state of disease. For instance, when a patient's SCNN1B protein level shows a general trend of increase over time, the patient is deemed to be improving in the severity of gastric cancer or the therapy the patient has been receiving is deemed effective. A lack of change in a patient's SCNN1B protein level or a continuing trend of decrease on other hand would indicate a worsening of the condition and ineffectiveness of the therapy given to the patient. Generally, a lower SCNN1B protein level seen in a patient indicates a more severe form of the gastric cancer the patient is suffering from and a worse prognosis of the disease, as manifested in shorter life expectancy, higher rate of metastasis, resistance to therapy etc. Among gastric cancer patients, one who has a lower level of SCNN1B protein expression in the gastric cancer sample than that found in a second gastric cancer patient has a higher likelihood of mortality compared to the second patient for any defined time period, such as 1-5 years post-diagnosis.

B. Preparing Samples for SCNN1B Protein Detection

The stomach tissue sample from a subject is suitable for the present invention and can be obtained by well-known methods and as described in the previous section. In certain applications of this invention, stomach mucosa may be the preferred sample type.

C. Determining the Level of Human SCNN1B Protein

A protein of any particular identity, such as SCNN1B protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human SCNN1B protein) can also be detected by gel electrophoresis (such as 2-dimensional gel electrophoresis) and western blot analysis using specific antibodies. Alternatively, standard immunohistochemical techniques can be used to detect a given protein (e.g., human SCNN1B protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human SCNN1B protein) can be generated by known techniques.

Other methods may also be employed for measuring the level of SCNN1B protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any stomach disease (especially any form of tumor such as gastric cancer) as conventionally defined is first selected. These individuals are within the appropriate parameters, if applicable, for the purpose of screening for and/or monitoring gastric cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human SCNN1B mRNA or SCNN1B protein in the stomach tissue sample obtained from the group can be reasonably regarded as representative of the normal or average level among the general population of healthy people. Preferably, the selected group comprises at least 10 human subjects.

Once an average value for the SCNN1B mRNA or protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of Gastric Cancer

By illustrating the correlation of suppressed expression of SCNN1B protein and gastric cancer, the present invention further provides a means for treating patients suffering from gastric cancer: by way of increasing SCNN1B protein expression or biological activity. As used herein, treatment of gastric cancer encompasses reducing, reversing, lessening, or eliminating one or more of the symptoms of gastric cancer, as well as preventing or delaying the onset of one or more of the relevant symptoms.

A. Increasing SCNN1B Expression or Activity

1. Nucleic Acids Encoding SCNN1B Proteins

Enhancement of SCNN1B gene expression can be achieved through the use of nucleic acids encoding a functional SCNN1B protein. Such nucleic acids can be single-stranded nucleic acids (such as mRNA) or double-stranded nucleic acids (such as DNA) that can translate into an active form of SCNN1B protein under favorable conditions.

In one embodiment, the SCNN1B-encoding nucleic acid is provided in the form of an expression cassette, typically recombinantly produced, having a promoter operably linked to the polynucleotide sequence encoding the SCNN1B protein. In some cases, the promoter is a universal promoter that directs gene expression in all or most tissue types; in other cases, the promoter is one that directs gene expression specifically in epithelial cells, especially in stomach epithelium. Administration of such nucleic acids can increase the SCNN1B protein expression in the target tissue, e.g., stomach epithelium. Since the human SCNN1B gene sequence encoding its mRNA is known as Genbank Accession No. NM_000336.2 and provided herein as SEQ ID NO:11, and its cDNA sequence is provided herein as SEQ ID NO:10, one can derive a suitable SCNN1B-encoding nucleic acid from the sequence, species homologs, and variants of these sequences.

2. SCNN1B Proteins

By directly administering an effective amount of an active SCNN1B protein to a patient suffering from gastric cancer and exhibiting suppressed SCNN1B protein expression or activity, the disease may also be effectively treated. For example, this can be achieved by administering a recombinantly produced SCNN1B protein possessing its biological activity to the patient suffering from gastric cancer. Formulations and methods for delivering a protein- or polypeptide-based therapeutic agent are well known in the art.

3. Activators of SCNN1B Protein

Increased SCNN1B protein activity can be achieved with an agent that is capable of activating the expression of SCNN1B protein or enhancing the activity of SCNN1B protein. For example, a demethylating agent (e.g., 5-Aza) may be able to activate SCNN1B gene expression by removing the suppression of SCNN1B gene expression caused by methylation of the promoter region of this gene. Other activating agents may include transcriptional activators specific for the SCNN1B promoter and/or enhancer. Such activating agents can be screened for and identified using the SCNN1B expression assays described in the examples herein.

Agonists of the SCNN1B protein, such as an activating antibody, are another kind of activators of the SCNN1B protein. Such activators act by enhancing the biological activity of the SCNN1B protein, typically (but not necessarily) by direct binding with the SCNN1B protein and/or its interacting proteins. Preliminary screening for such agonists may start with a binding assay for identifying molecules that physically interact with SCNN1B protein.

B. Pharmaceutical Compositions

1. Formulations

Compounds of the present invention are useful in the manufacture of a pharmaceutical composition or a medicament. A pharmaceutical composition or medicament can be administered to a subject for the treatment of gastric cancer. Compounds used in the present invention, e.g., a SCNN1B protein, a nucleic acid encoding SCNN1B protein, or an activator of SCNN1B gene expression, are useful in the manufacture of a pharmaceutical composition or a medicament comprising an effective amount thereof in conjunction or mixture with excipients or carriers suitable for application.

An exemplary pharmaceutical composition for enhancing SCNN1B expression comprises (i) an express cassette comprising a polynucleotide sequence encoding a human SCNN1B protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

A SCNN1B protein or a nucleic acid encoding a SCNN1B protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., skin cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a SCNN1B protein or a nucleic acid encoding a SCNN1B protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a SCNN1B protein or a nucleic acid encoding a SCNN1B protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of SCNN1B protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control gastric cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of SCNN1B protein or nucleic acid encoding a SCNN1B protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for SCNN1B protein or a nucleic acid encoding a SCNN1B protein described herein are provided. Dosage for a SCNN1B-encoding nucleic acid, such as an expression cassette, can be between 0.1-0.5 mg/eye, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. SCNN1B Protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a SCNN1B protein or a nucleic acid encoding the protein). The additional therapeutic compound can also be administered separately, in a separate composition, or a different dosage form from the main active ingredient. Some doses of the main ingredient, such as a SCNN1B protein or a nucleic acid encoding a SCNN1B protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of SCNN1B mRNA or SCNN1B protein in a subject, which can be used for various purposes such as detecting or diagnosing the presence of gastric cancer, determining the risk of developing gastric cancer, and monitoring the progression of gastric cancer in a patient, including assessing the likelihood of mortality from gastric cancer.

Kits for carrying out assays for determining SCNN1B mRNA level typically include at least one oligonucleotide useful for specific hybridization with at least one segment of the SCNN1B coding sequence or its complementary sequence. Optionally, this oligonucleotide is labeled with a detectable moiety. In some cases, the kits may include at least two oligonucleotide primers that can be used in the amplification of at least one segment of SCNN1B DNA or mRNA by PCR, particularly by RT-PCR.

Kits for carrying out assays for determining SCNN1B protein level typically include at least one antibody useful for specific binding to the SCNN1B protein amino acid sequence. Optionally, this antibody is labeled with a detectable moiety. The antibody can be either a monoclonal antibody or a polyclonal antibody. In some cases, the kits may include at least two different antibodies, one for specific binding to the SCNN1B protein (i.e., the primary antibody) and the other for detection of the primary antibody (i.e., the secondary antibody), which is often attached to a detectable moiety.

Typically, the kits also include an appropriate standard control. The standard controls indicate the average value of SCNN1B protein or mRNA in the stomach epithelium of healthy subjects not suffering from gastric cancer. In some cases such standard control may be provided in the form of a set value. In addition, the kits of this invention may provide instruction manuals to guide users in analyzing test samples and assessing the presence, risk, or state of gastric cancer in a test subject.

In a further aspect, the present invention can also be embodied in a device or a system comprising one or more such devices, which is capable of carrying out all or some of the method steps described herein. For instance, in some cases, the device or system performs the following steps upon receiving a stomach tissue sample, e.g., a stomach mucosa sample taken from a subject being tested for detecting gastric cancer, assessing the risk of developing gastric cancer, or monitored for progression of the condition: (a) determining in sample the amount or concentration of SCNN1B mRNA, SCNN1B protein; (b) comparing the amount or concentration with a standard control value; and (c) providing an output indicating whether gastric cancer is present in the subject or whether the subject is at risk of developing gastric cancer, or whether there is a change, i.e., worsening or improvement, in the subject's gastric cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Introduction

The current invention is based on the identification of the tumor suppressor gene SCNN1B and its role in gastric cancer. Protein expression and promoter methylation of this SCNN1B can serve as new diagnostic markers as well as to provide prognostic information relating to the survival of gastric cancer patients who have been diagnosed with the disease.

Gastric cancer is the fifth leading cause of cancer and the third leading cause of cancer-related mortality globally. The prognosis of patients with gastric cancer continues to be dismal, despite improving surgical and adjuvant treatment approaches, with a 5-year overall survival less than 25% (Camargo M C, Kim W H, Chiaravalli A M, Kim K M, Corvalan A H, Matsuo K, Yu J, Sung J J, Herrera-Goepfert R, Meneses-Gonzalez F, Kijima Y, Natsugoe S, Liao L M, Lissowska J, Kim S, Hu N, Gonzalez C A, Yatabe Y, Koriyama C, Hewitt S M, Akiba S, Gulley M L, Taylor P R, Rabkin C S. Improved survival of gastric cancer with tumour Epstein-Barr virus positivity: an international pooled analysis. *Gut* 2014; 63: 236-43). There is emerging evidence indicating that epigenetic alterations of tumor-related genes, especially inactivation of tumor suppressor genes by promoter hypermethylation, contributes a lot to the development of gastric cancer (Choi I S, Wu T T. Epigenetic alterations in gastric carcinogenesis. *Cell Res,* 2005; 15: 247-54). Identification of novel genes silenced by promoter hypermethylation in gastric cancer is very important for the identification of new markers and therapeutic targets for diagnosis and treatment of this disease. Using the Infinium HumanMethylation450 BeadChip Kit for screening hypermethylated candidates in gastric cancer, the gene Sodium channel, non-voltage gated 1 beta subunit (SCNN1B), function of which remains largely uncharacterized in cancer, was identified to be preferentially methylated in gastric cancer. Inactivation of SCNN1B by epigenetic mechanism may play a role during gastric carcinogenesis.

The present inventors revealed that SCNN1B was down-regulated by promoter methylation in gastric cancer cells, and that SCNN1B was also down-regulated by promoter methylation in primary gastric tumors. Restoration of SCNN1B expression inhibits cancer cell growth and induces programmed cell death mediated by certain molecular regulators.

The clinical application of SCNN1B was evaluated in this study. SCNN1B methylation was analyzed in a cohort of paired primary gastric cancer and adjacent normal tissues from Hong Kong (n=64). BGS analysis showed that methylation levels in gastric tumors were higher as compared to adjacent normal tissues. Kaplan-Meier survival curves showed that gastric cancer patients with SCNN1B methylation in adjacent normal tissues have a significantly shorter survival than those without methylation (log-rank test: p=0.039). These data indicate that the propensity for SCNN1B methylation indicates more aggressive disease.

The association of SCNN1B protein expression with clinicopathological features and clinical outcome were evaluated utilizing a gastric cancer tissue microarray (n=245). SCNN1B cytoplasmic expression showed a significant correlation with TNM stage (p<0.001) and lymphatic metastasis (p=0.036), but had no correlation with age, gender, *H. pylori* infection, histology or tumor differentiation. In univariate analysis, a moderate or high cytoplasmic SCNN1B score was associated with better disease specific survival by univariate Cox regression analysis (Moderate: RR: 0.482, 95% CI: 0.320 to 0.726, p<0.001; High: RR: 0.247, 95% CI: 0.091 to 0.674, p=0.006). Apart from SCNN1B expression, age (p=0.048), histology with diffuse (p=0.004) or mixed component (p<0.001) and TNM staging (p<0.001) was also correlated with survival by univariate analysis. After adjustment for potential confounding factors such as age, gender, histology, tumor differentiation and TNM stage, SCNN1B expression was found to be independent prognostic factor for disease-specific survival (Moderate: RR: 0.547, 95% CI: 0.360 to 0.829, p=0.005; High: RR: 0.353, 95% CI: 0.128 to 0.971, p=0.044) by multivariate Cox proportional hazards regression analysis. Further stratification of the cohort into early stage (TNM stage I-III) and late stage (TNM stage IV) revealed that expression of SCNN1B was associated with better survival in early stage gastric cancer. As shown by Kaplan-Meier curves, patients with high or moderate SCNN1B expression had significantly longer survival in the overall (p<0.001) and stage I-III (p<0.001), but not in stage IV (p=0.434). These findings indicate that high SCNN1B expression predicts a favorable prognosis in patients in gastric cancer especially in the early stages.

In brief, the tumor suppressive function of SCNN1B could potentially be applied to therapeutic intervention. Protein expression and methylation status of SCNN1B closely relate to the survival of gastric cancer patients especially in early stage and can be used as new prognostic markers for gastric cancer. Utilizing this information, individual who are deemed to have an increased likelihood of developing gastric cancer (e.g., due to family history or environmental risk factors) could be screened regularly for early detection of the disease. Diagnosis of gastric cancer at its earlier stages allows for patients a broader ranges of choices in terms of effective and appropriate therapeutic methods including but not limited to surgical intervention, chemotherapy, and radiotherapy, so as to improve patients' chances of long term survival from this deadly disease.

Materials and Methods

Human Gastric Specimens

Tissue Samples

Surgically excised gastric cancer tissues and surrounding non-tumor gastric tissues were obtained from 104 gastric cancer patients from the Chinese University of Hong Kong. Tumor was staged according to the TNM staging system. Patients were being regularly followed up and the median follow-up duration since the time of diagnosis was 16.8 months (range 0 to 136.3 months). For tissue microarray, a total of 264 gastric cancer samples were retrieved from the tissue bank of Anatomical and Cellular Pathology, Prince of Wales Hospital, Hong Kong from 1998 to 2006. The 264 samples were embedded into tissue microarray blocks. Written consent forms were obtained prior to tissue collection. The study was approved by the Clinical Research Ethics Committee of the Chinese University of Hong Kong.

Tumor Cell Line

Sixteen gastric cell lines (AGS, BGC823, HGC27, KATOIII, MGC803, MKN1, MKN7, MKN28, MKN45, MKN74, NCI-N87, SGC7901, SNU1, SNU638, SNU719, and YCC10) were obtained from the American Type Culture Collection (ATCC, Manassas, Va.), Riken Gene Bank (RIKEN BioResource Center, Ibaraki, Japan), Dr Sun Young Rha (Yonsei Cancer Center, Yonsei University College of Medicine, Seoul, Korea), or Beijing Oncology Hospital, Beijing, China. The cells were cultured in RPMI 1640 medium (Gibco BRL, Rockville, Md.) supplemented with 10-20% fetal bovine serum (Gibco BRL). All cells were incubated with 5% of $CO_2$ at 37° C.

Gene Expression Analysis

RNA Isolation

Total RNA was isolated using Qiazol reagent (Qiagen, Valencia, Calif., USA). First, about $5-10 \times 10^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring absorbance at 260 nm/280 nm using NanoDrop ND-1000 (NanoDrop Technologies, Wilmington, Del., USA). The purified RNA was store at −80° C. until using.

cDNA Synthesis

High-Capacity cDNA Reverse Transcription Kit (Applied Biosystems, Foster City, Calif., USA) was used to synthesize cDNA. The reaction mixture contained 1×Reverse Transcriptase buffer, 1×dNTP, 1×random primer (supplied by kit), 2.5 U/µL reverse transcriptase, 1 U/µL RNase inhibitor and 2 µg total RNA. The mixture was incubated at 25° C. for 10 min, then 37° C. for 120 min, then 85° C. 5 min to inactivate the enzymes. The cDNA was stored at −80° C. until other application.

Semiquantitative Reverse Transcription PCR (RT-PCR)

Semiquantitative RT-PCR was performed in a total volume of 25 µL reaction containing 1× Premix Ex Taq (Takara, Ohtsu, Japan) and 5-10 ng cDNA. The PCR program started with an initial denaturation at 95° C. for 10 min, followed by 27-35 cycles (95° C. for 30 sec, annealing temperature for 30 sec, and 72° C. for 30 sec) of amplification, with a final extension at 72° C. for 10 min. The PCR bands were visualized under ultraviolet light and photographed. The expression of the target gene was normalized by the expression of house-keeping gene β-actin, which served as an internal control. All primers used to amplify the transcripts are listed in Table 1.

Immunohistochemistry

Paired primary tumor and adjacent non-tumor samples were obtained from 10 gastric cancer patients after surgical resection. Tissue types (tumor or normal) were assessed by histological staining. The remaining tissue specimens were fixed in 10% of formalin and embedded in paraffin. Immunohistochemistry was performed on five-micrometer paraffin sections using anti-SCNN1B antibody (HPA015612, Sigma-Aldrich) with dilution of 1:200. The percentages of cells with positive labeling were used as immunohistochemical scores. The ethics committee of the Chinese University of Hong Kong approved of this study, and written consents were obtained from all patients involved.

DNA Methylation Analysis

Genomic DNA Extraction

Genomic DNA from gastric cancer cell lines and tissue samples were isolated by using DNA mini kit (Qiagen) according to the kit protocol. About 25 mg samples were lysed in 180 µL of QIAamp ATL buffer and 20 µL of proteinase K in a 1.5 mL microcentrifuge tubes for 1 hour at 56° C. Four microliter of RNase A (100 mg/ml, Qiagen) was added and mixed by pulse-vortexing for 15 s followed by 2 min incubation at room temperature. Then 200 µL of AL buffer was added to the lysate and samples were incubated for 10 min at 70° C. After adding 200 µL of absolute ethanol, the solution was mixed by pulse-vortexing for 15 s. Then lysates were purified over a QIAamp column as specified by the manufacturer. The genomic DNA was diluted in 200 µL DNase-free $H_2O$. The quality and quantity of DNA were determined by measuring absorbance at 260 nm/280 nm using NanoDrop ND-1000 (NanoDrop).

Sodium Bisulfite Conversion

The genomic DNA was modified by sodium metabisulfite. Briefly, 5 µg genomic DNA in 30 µL TE buffer (Sigma-Aldrich) was mixed with 3.3 µL of 3 mM NaOH to a final concentration of 0.3 mM and incubate at 37° C. for 15 min. Denatured DNA was mixed with 333 µL of bisulfite solution and treated in darkness for 4 hr at 55° C. The bisulfite solution was prepared as 2.4 M sodium metabisulfite (pH 5.0-5.2) (Sigma-Aldrich) and 0.5 mM hydroquinone (Sigma-Aldrich). The treated DNA was desalted and purified using the Qiaex II kit (Qiagen) according to the protocol supplied by the kit. DNA was then treated with 0.3 M NaOH at 37° C. for 15 min and precipitated with 3 M ammonium acetate and 3 volumes of ethanol. Recovered DNA was dissolved in 100 µL TE buffer (pH 8.0) and stored at −20° C.

Demethylation Treatment Using 5-Aza-2'-Deoxycytidine ("5-Aza")

Cells were seeded at a density of $1 \times 10^5$/100-mm dishes and grew for 24 hr. Cells were then treated with 10 µM 5-aza-2'-deoxycytidine ("5-Aza") (Sigma-Aldrich) for 5 days. The 5-Aza was replenished every day. The gene expression of SCNN1B was evaluated using semiquantitative RT-PCR.

Direct Bisulfite Genomic Sequencing (BGS)

Bisulfite treated DNA was amplified with primers listed in Table 1. In one example, bisulfite treated DNA was PCR-amplified with the following BGS primers: forward 5'-GTT-TAGTGTTTTTGAATTTGG-3' (SEQ ID NO:3) and reverse CTTCTACACCCTAAAAACTTTTCC-3' (SEQ ID NO:4). PCR amplification with 2 µL of bisulfite-treated DNA gives a PCR product of about 550 bp, containing 58 CpG dinucleotides at the SCNN1B promoter region. Amplified BGS products were sequenced. Sequencing analysis was performed by SeqScape software (Applied Biosystems, Foster City, Calif.). Methylation percentage of each CpG site was calculated according this formula: Methylation %=$H_C$/($H_C$+$H_T$)×100%, ($H_C$=Height of peak C, $H_T$=Height of peak T).

Biological Function Analysis

Cloning of SCNN1B and Construction of Expression Vector

The full-length cDNA of SCNN1B gene expression vector was generated by PCR-cloning. Total RNA from human gastric tissue (Ambion, Austin, Tex., USA) was reverse transcribed into cDNA. Sequence corresponding to the open reading frame (ORF) of SCNN1B was amplified by PCR. PCR product was cloned into the pCDNA3.1 expression vector.

SCNN1B Gene Transfection

Cells were seeded at ~6×10$^5$ cells on a 6-well plate without antibiotics for about 24 hr till the cell density reached about 90% confluent. Cells were then transfected with 2 µg SCNN1B and control vector (pCDNA3.1) respectively using Lipofectamine 2000 (Invitrogen). Lipofectamine 2000 (6.0 µL) diluted in 125 µL Opti-MEM (Invitrogen) was incubate at room temperature for 5 min. Then, plasmid DNA diluted in 125 µL Opti-MEM was combined with the Lipofectamine mixture. After 24~48 hr incubation at 37° C. in a 5% $CO_2$ incubator, cells were harvested for testing of transgenic expression. For stable cell lines, cells were passaged at a 1:10 ratio into fresh growth medium with proper concentration of neomycin (G418) (Invitrogen). Stable transfection cells were harvested after 14-21 days of selection.

Cell Viability Assay

Cell viability of stably transfected cells was examined using the MTT Cell viability Assay Kit (Sigma-Aldrich) according to the manufacturer's instructions. All experiments were conducted three times in triplicates. Results were shown as the means±SD.

Colony Formation Assay

Cells were seeded at 500 to 2000 cells on a 6-well plate. After 7-14 days, cells were stained with 0.5% crystal violet solution. Colony with more than 50 cells per colony was counted. The experiment was conducted in three independent triplicates.

Annexin V Apoptosis Assay

Annexin V is a protein that could bind the cell membrane after apoptosis have occurred and before membrane integrity has been lost. The proportion of apoptotic cells was evaluated using Annexin V and 7-amino-actinomycin (7-AAD) double staining. Briefly, the cells washed with 1×PBS was resuspended in 100 µL ice-cold annexin-binding buffer (10 mM HEPES, 140 mM NaCl and 2.5 mM CaCl2, pH 7.4) containing 5 µL Annexin V conjugated with PE (Invitrogen) and 2 µL 7-AAD staining. After incubation for 15 min at room temperature, cells were mixed with additional 400 µL of ice-cold annexin-binding buffer and analyzed using flow cytometry.

Cell Cycle Analysis

The cells were fixed in 70% ethanol-PBS for 24 hours. The cells were then labeled with 50 µg/ml of propidium iodide (BD Pharmingen, Franklin Lakes, N.J.). The cells were sorted by FACSCalibur (BD Biosciences, San Diego, Calif.). Cell-cycle profiles were analyzed by Flowjo software (Treestar, Inc., San Carlos, Calif.). All experiments were conducted three times in triplicates.

Flow Cytometry

The proportion of apoptotic cells was evaluated using Annexin V and 7-amino-actinomycin (7-AAD) double staining assay. Briefly, the cells washed with 1×PBS was resuspended in 100 µL ice-cold annexin-binding buffer (10 mM HEPES, 140 mM NaCl and 2.5 mM CaCl2, pH 7.4) containing 5 µL Annexin V conjugated with PE (Invitrogen) and 2 µL 7-AAD staining. After incubation for 15 min at room temperature, cells were mixed with additional 400 µL of ice-cold Annexin-binding buffer and analyzed using flow cytometry.

For cell cycle analysis, the cells were fixed in 70% ethanol-PBS for 24 hours. The cells were then labeled with 50 µg/ml of propidium iodide (BD Pharmingen, Franklin Lakes, N.J.). The cells were sorted by FACSCalibur (BD Biosciences, San Diego, Calif.). Cell-cycle profiles were analyzed by Flowjo software (Treestar, Inc., San Carlos, Calif.). All experiments were conducted three times in triplicates.

In Vivo Tumorigenicity

For in vivo tumorigenicity assay, 5×10$^6$ empty vector- or SCNN1B-transfected cells were injected subcutaneously into dorsal right flank of 4-week-old male Balb/c nude mice (five mice per group). Tumor volume was measured every 3 days over a 3-week period. Tumor volume (mm$^3$) was estimated by measuring the longest and shortest diameter of the tumor (Formula: Volume=0.5×Length×2×Width). Mice were sacrificed at 3 weeks after injection. Tumors were excised and weighed. The excised tissues were either fixed in 10% neutral-buffered formalin or snap frozen in liquid nitrogen. Tumor sections from paraffin-embedded blocks were used for histologic examination. All animal studies were performed in accordance with guidelines approved by the Animal Experimentation Ethics Committee of The Chinese University of Hong Kong.

Statistical Analysis

The results were expressed as mean±SD. The Manne-Whitney U test was performed to compare the difference of SCNN1B protein expression between tumor and adjacent non-tumor tissues. The difference in tumor growth rate between the two groups of nude mice was determined by repeated-measures analysis of variance. The Chi-Squared test was used for comparison of patient characteristics and distributions of methylation and covariates by vital status. Patient age (at entry to follow-up) by vital status was compared using the t test. Crude RRs of recurrence associated with SCNN1B methylation and protein expression were first estimated using the univariate Cox proportional hazards regression model. A multivariate Cox model was constructed to estimate adjusted RR for SCNN1B protein expression. Disease-specific survival in relation to protein expression status was evaluated by the Kaplan-Meier curve and the log-rank test. A P-value<0.05 was regarded as statistically significant.

Results

Figure 2:
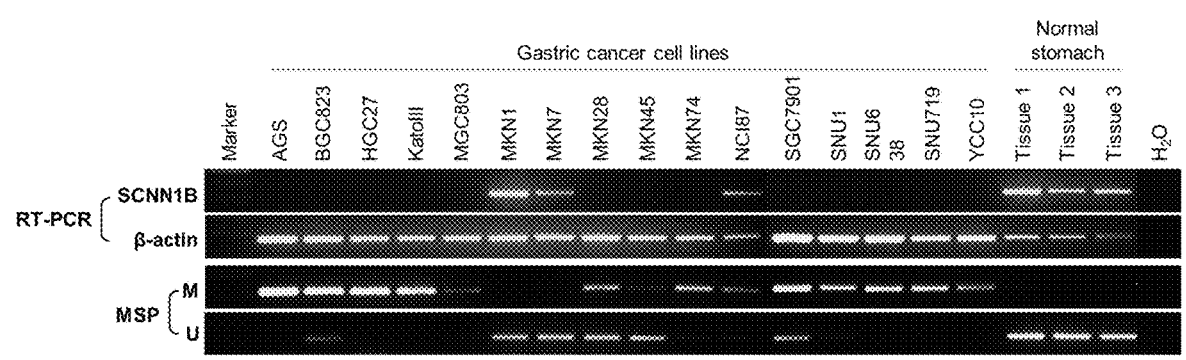
FIG. 2 shows SCNN1B mRNA expression in normal tissues and gastric cell lines in an embodiment.

Silence or Down-Regulation of SCNN1B in Gastric Cancer
SCNN1B is Down-Regulated in Primary Gastric Tumors
SCNN1B mRNA expression was significantly down-regulated of gastric tumor tissues compared with their adjacent non-tumor tissues (P<0.0001; FIG. 1A). Consistently, SCNN1B protein level was reduced in gastric tumor tissues compared with their adjacent non-tumor tissues (P<0.005; Figure. 1B). Moreover, SCNN1B expression silenced in 13 out of 16 cell lines tested (Figure. 2). These results indicated an aberrant down-regulation of SCNN1B in gastric cancer.

SCNN1B Promoter is Methylated in Gastric Cancer

Figure 3:
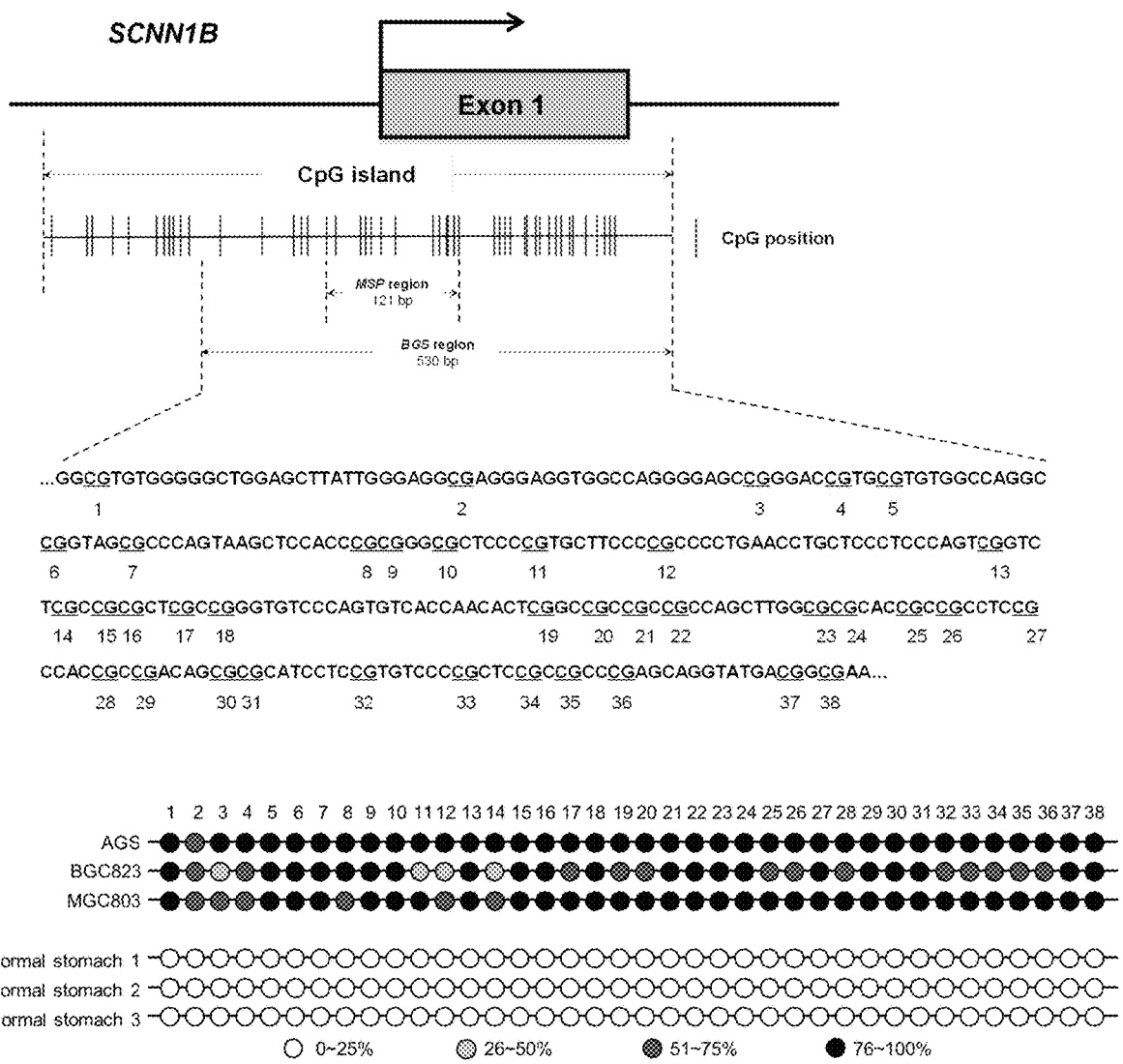
FIG. 3 shows bisulfate genomic sequencing results of SCNN1B promoter in gastric cancer cell lines in an embodiment (CpG island contains SEQ ID NO:13).

To determine the role of promoter methylation in silencing of SCNN1B, its promoter methylation was evaluated by methylation-specific PCR (MSP) and bisulfite genomic sequencing (BGS). MSP analysis revealed SCNN1B promoter methylation in all cell lines with silenced SCNN1B (FIG. 2). BGS analysis of 38 CpG sites in SCNN1B promoter showed dense methylation in the majority of gastric cancer cells examined, except for SCNN1B-expressing MKN1 cells; whereas normal gastric tissues did not show significant SCNN1B promoter methylation (FIG. 3).

SCNN1B Expression could be Restored after Demethylation Treatment

Figure 4:
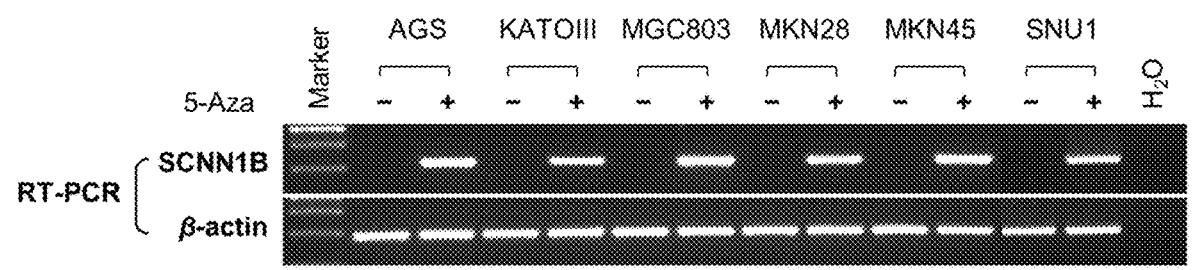
FIG. 4 shows the effect of a demethylating agent on SCNN1B expression in an embodiment.

To test whether methylation directly mediates SCNN1B silencing, six gastric cancer cell lines (AGS, KATOIII, MGC803, MKN28, MKN45 and SNU1) with silenced SCNN1B expression were treated with the DNA methyltransferase inhibitor 5-Aza. Restored expression of SCNN1B was observed in all of these cell cells (FIG. 4).

Functional Assay

Inhibition of Cell Proliferation by SCNN1B

Figure 5:
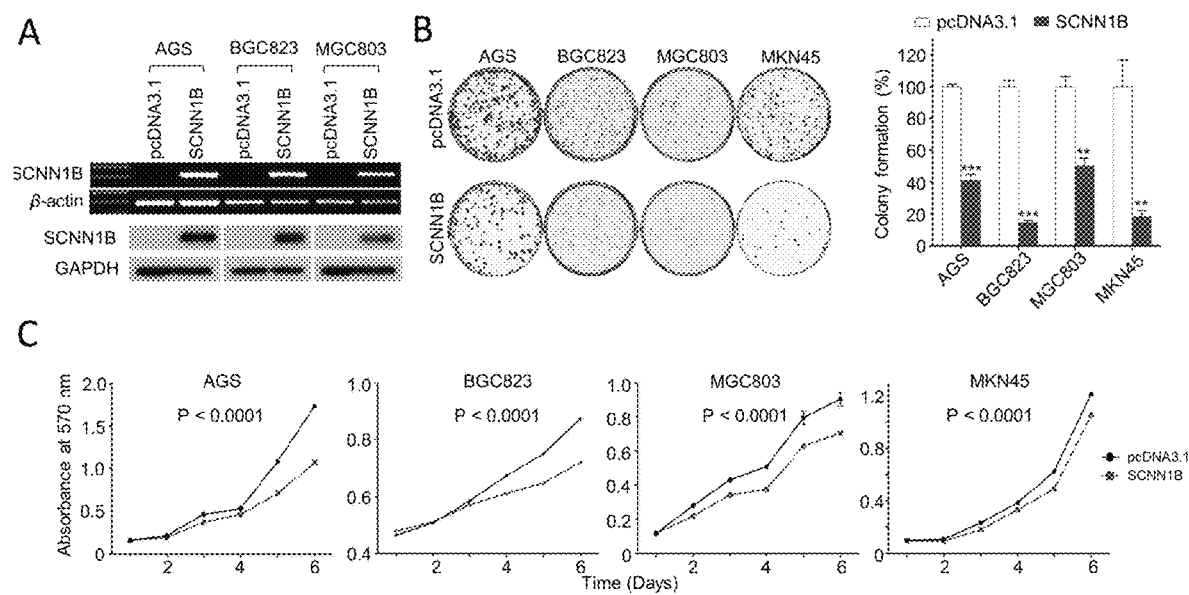
FIG. 5 shows SCNN1B inhibited gastric cancer cell growth in an embodiment.

The frequent silencing of SCNN1B in gastric cancer cell lines and tissues suggested that SCNN1B may have a tumor suppressive function. To prove this, four stably transfected cell lines (AGS, BGC823, MGC803 and MKN45) with SCNN1B over-expression were generated. SCNN1B ectopic expression was verified by RT-PCR and Western blot, respectively (FIG. 5A). Ectopic expression of SCNN1B significantly reduced the number of colonies formed in SCNN1B-transfected AGS, BGC823, MGC803 and MKN45 cells compared to empty vector transfected controls (FIG. 5B). SCNN1B expression also significantly inhibited cell viability in AGS, BGC823, MGC803 and MKN45 cells (FIG. 5C). These results indicated that SCNN1B was important for inhibiting gastric cancer cell growth.

SCNN1B Induced Cell Apoptosis and Cell Cycle Arrest

Figure 6:
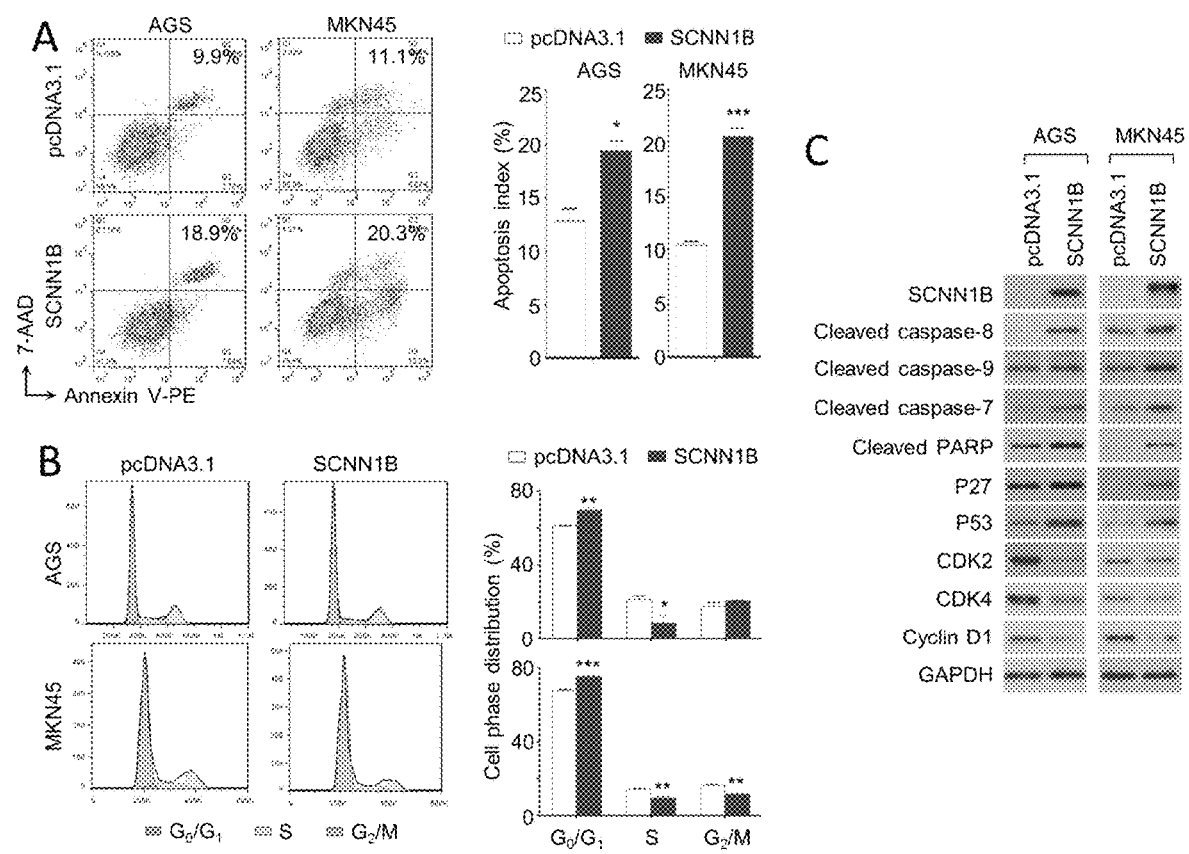
FIG. 6 shows SCNN1B arrest cells in G1 phase and induced cell apoptosis in an embodiment.

To determine the mechanism by which SCNN1B inhibited cell growth, the effect of SCNN1B on cell apoptosis was analyzed by flow cytometry with Annexin V-PE and 7-AAD double staining. The result showed an increase in the number of apoptotic cells in SCNN1B-transfected AGS cells compared to vector-transfected AGS cells. A similar effect was observed in SCNN1B-transfected MKN45 cells (FIG. 6A). The expression of apoptosis markers cleaved caspase-8, caspase-9, caspase-7 and PARP was increased, consistent with the induction of apoptosis.

The effect of SCNN1B on cell cycle distribution was next analyzed by flow cytometry. Ectopic expression of SCNN1B in gastric cancer cells led to a significant increase in the G1 phase population, and a corresponding reduction in the S phase population (FIG. 6B). Consistently, SCNN1B enhanced protein expression of G1 gatekeepers $p21^{Cip1}$ and p53; while reduced the expression of G1 cell cycle promoting factors cyclin D1, CDK2 and CDK4 (Figure. 6C). These results indicated that SCNN1B acted on G1/S checkpoint to prohibit cell cycle in gastric cancer cells.

In Vivo Tumor Suppression

Figure 7:
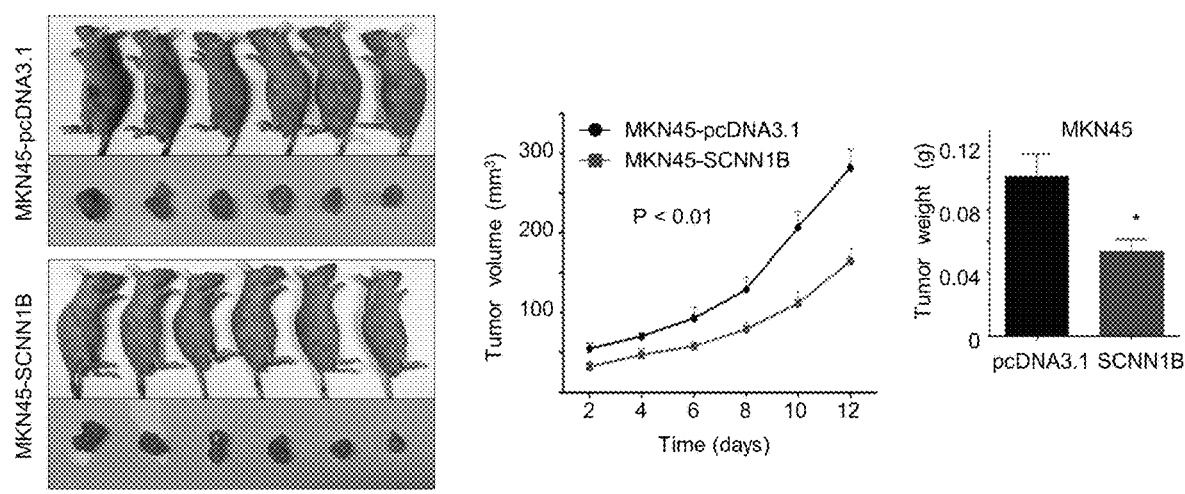
FIG. 7 shows SCNN1B inhibited tumorigenesis in vivo in an embodiment.
Figure 8:
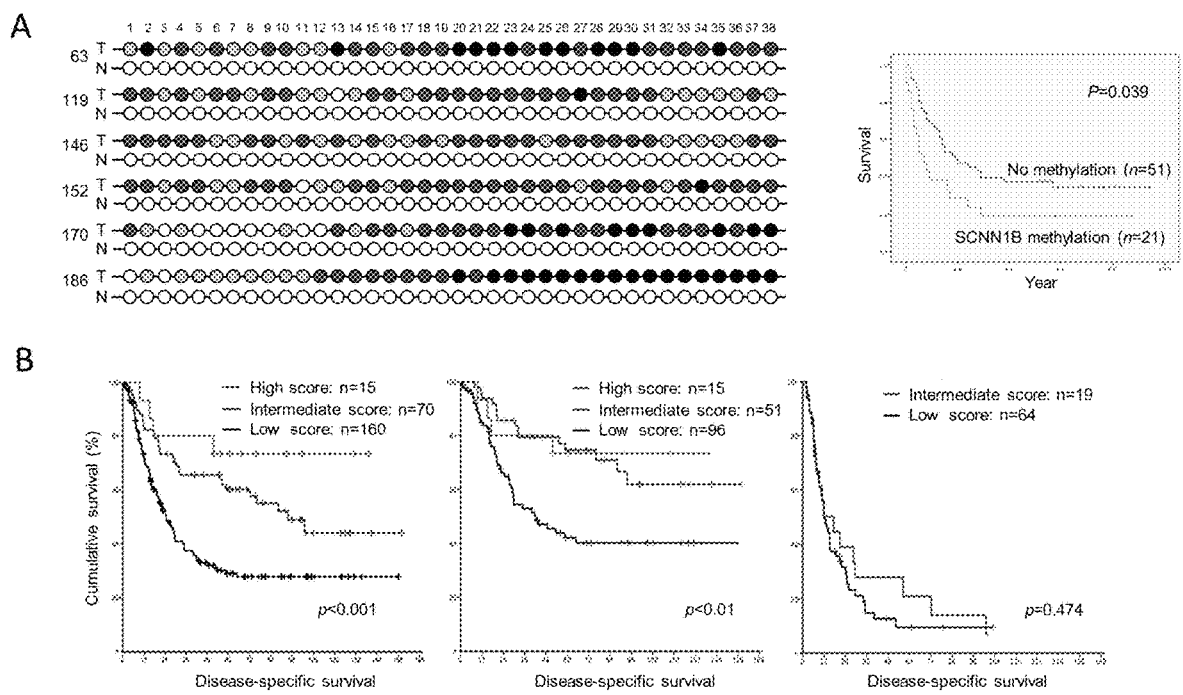
FIG. 8 shows methylation and protein expression of SCNN1B served as predictors of gastric cancer prognosis.

To further explore the in vivo tumourigenic ability of CA4, empty vector- and SCNN1B-transfected MKN45 cells were injected into the right flanks of nude mice respectively. The tumor growth rate in nude mice injected with MKN45-SCNN1B cells was significantly slower than that with MKN45-vector control cells (FIG. 7). Twelfth days after injection, mice were sacrificed and xenografts were excised. The average tumor weight in nude mice injected with MKN45-SCNN1B was significantly lower compared to that in control mice (P<0.01, FIG. 7).

SCNN1B Promoter Methylation Status in Gastric Cancer

To evaluate the clinical significance of SCNN1B promoter methylation, SCNN1B methylation was analyzed in a cohort of paired primary gastric cancer and adjacent normal tissues from Hong Kong (n=64). BGS analysis showed that methylation levels in gastric tumors were higher as compared to adjacent normal tissues. Kaplan-Meier survival curves showed that gastric cancer patients with SCNN1B methylation in adjacent normal tissues have a significantly shorter survival than those without methylation (log-rank test: p=0.039). The data show that the propensity for SCNN1B methylation indicates more aggressive disease.

SCNN1B Expression Status in Gastric Cancer

To evaluate the association of SCNN1B expression with clinicopathological features and clinical outcomes, the SCNN1B protein expression in gastric cancer was assessed, utilizing a gastric cancer tissue microarray (n=245). SCNN1B cytoplasmic expression showed a significant correlation with TNM stage (p<0.001) and lymphatic metastasis (p=0.036), but had no correlation with age, gender, *H. pylori* infection, histology or tumor differentiation. In univariate analysis, a moderate or high cytoplasmic SCNN1B score was associated with better disease specific survival by univariate Cox regression analysis (Moderate: RR: 0.482, 95% CI: 0.320 to 0.726, p<0.001; High: RR: 0.247, 95% CI: 0.091 to 0.674, p=0.006). Apart from SCNN1B expression, age (p=0.048), histology with diffuse (p=0.004) or mixed component (p<0.001) and TNM staging (p<0.001) was also correlated with survival by univariate analysis. After adjustment for potential confounding factors such as age, gender, histology, tumor differentiation and TNM stage, SCNN1B expression was found to be independent prognostic factor for disease-specific survival (Moderate: RR: 0.547, 95% CI: 0.360 to 0.829, p=0.005; High: RR: 0.353, 95% CI: 0.128 to 0.971, p=0.044) by multivariate Cox proportional hazards regression analysis. Further stratification of the cohort into early stage (TNM stage I-III) and late stage (TNM stage IV) revealed that expression of SCNN1B was associated with better survival in early stage gastric cancer. As shown by Kaplan-Meier curves, patients with high or moderate SCNN1B expression had significantly longer survival in the overall (p<0.001) and stage I-III (p<0.001), but not in stage IV (p=0.434). These findings indicate that high SCNN1B expression predicts a favorable prognosis in patients in gastric cancer especially in the early stages.

All patents, patent applications, and other publications, including GenBank Accession Numbers, cited in this application are incorporated by reference in the entirety for all purposes.

TABLE 1

DNA sequences of primers used in this study

| Primer name | Sequence (5'-3') | |
|---|---|---|
| A) RT-PCR primers for detecting SCNN1B mRNA expression: | | |
| SCNN1B-F | AGACAACCACAATGGCTTAACA | SEQ ID NO: 1 |
| SCNN1B-R | TGAGGCTACATAGTCTCATGGC | SEQ ID NO: 2 |
| B) BGS primers: | | |
| SCNN1B- BGS-F | GTTTAGTGTTTTTGAATTTGG | SEQ ID NO: 3 |
| SCNN1B- BGS-R | CTTCTACACCCTAAAAACTTTTCC | SEQ ID NO: 4 |

TABLE 1-continued

DNA sequences of primers used in this study

| Primer name | Sequence (5'-3') | |
|---|---|---|
| *C) MSP primers:* | | |
| SCNN1B-MSP-MF | GTGTGGTTAGGTCGGTAGC | SEQ ID NO: 5 |
| SCNN1B-MSP-MR | AACACTAAAACACCCGACG | SEQ ID NO: 6 |
| SCNN1B-MSP-UF | GTGTGGTTAGGTTGGTAGT | SEQ ID NO: 7 |
| SCNN1B-MSP-UR | AACACTAAAACACCCAACA | SEQ ID NO: 8 |

TABLE 2

Target sequences used in this study

1) SEQ ID NO: 9: Sequence of promoter region of human SCNN1B gene (−132 to +400 from the transcription start site)
GTTTAGTGTTTTTGAATTTGGTGTGTGGGGGTTGGAGTTTATTGGGAGGT
GAGGGAGGTGGTTAGGGAGGTTGGGATTGTGTGTGTGGTTAGGTTGGTAG
TGTTTAGTAAGTTTTATTTGTGGGTGTTTTTTGTGTTTTTTTGTTTTTGA
ATTTGTTTTTTTTTAGTTGGTTTTGTTGTGTTTGTTGGGTGTTTTAGTGT
TATTAATATTTGGTTGTTGTTGTTAGTTTGGTGTGTATTGTTGTTTTTGT
TATTGTTGATAGTGTGTATTTTTTGTGTTTTTGTTTTGTTGTTTGAGTAG
GTATGATGGTGAATTTTGGTTTGTATTTGGTTTTTTGTGTGTTGTTTGGA
GTTTTTGTGTGTGTGTTTTTTTTTGTTTAATTTTGGTTTGTGAGTTTTTG
TTTTGGTTTTAGTTTTTTATGGGAGGGTGTTTGGGTGTTTGTTTGAGGTG
TTTGGGATTTGGTTTGGGGATTGAATGGGTTGGGGGTGGAGGGGAGAGTT
GGAGGTTGGGAAAAGTTTTTAGGGTGTAGAAG 2) SEQ ID NO: 10: SCNN1B protein coding cDNA sequence (1923 bp)
ATGCACGTGAAGAAGTACCTGCTGAAGGGCCTGCATCGGCTGCAGAAGGG
CCCCGGCTACACGTACAAGGAGCTGCTGGTGTGGTACTGCGACAACACCA
ACACCCACGGCCCCAAGCGCATCATCTGTGAGGGCCCCAAGAAGAAAGCC
ATGTGGTTCCTGCTCACCCTGCTCTTCGCGCCCTCGTCTGCTGGCAGTG
GGGCATCTTCATCAGGACCTACTTGAGCTGGGAGGTCAGCGTCTCCCTCT
CCGTAGGCTTCAAGACCATGGACTTCCCTGCCGTCACCATCTGCAATGCT
AGCCCCTTCAAGTATTCCAAAATCAAGCATTTGCTGAAGGACCTGGATGA
GCTGATGGAAGCTGTCCTGGAGAGAATCCTGGCTCCTGAGCTAAGCCATG
CCAATGCCACCAGGAACCTGAACTTCTCCATCTGGAACCACACACCCCTG
GTCCTTATTGATGAACGGAACCCCCACCACCCCATGGTCCTTGATCTCTT
TGGAGACAACCACAATGGCTTAACAAGCAGCTCAGCATCAGAAAAGATCT
GTAATGCCCACGGGTGCAAAATGGCCATGAGACTATGTAGCCTCAACAGG
ACCCAGTGTACCTTCCGGAACTTCACCAGTGCTACCCAGGCATTGACAGA
GTGGTACATCCTGCAGGCCACCAACATCTTTGCACAGGTGCCACAGCAGG
AGCTAGTAGAGATGAGCTACCCCGGCGAGCAGATGATCCTGGCCTGCCTA
TTCGGAGCTGAGCCCTGCAACTACCGGAACTTCACGTCCATCTTCTACCC
TCACTATGGCAACTGTTACATCTTCAACTGGGGCATGACAGAGAAGGCAC
TTCCTTCGGCCAACCCTGGAACTGAATTCGGCCTGAAGTTGATCCTGGAC
ATAGGCCAGGAAGACTACGTCCCCTTCCTTGCGTCCACGGCCGGGGTCAG
GCTGATGCTTCACGAGCAGAGGTCATACCCCTTCATCAGAGATGAGGGCA
TCTACGCCATGTCGGGGACAGAGACGTCCATCGGGGTACTCGTGGACAAG
CTTCAGCGCATGGGGGAGCCCTACAGCCCGTGCACCGTGAATGGTTCTGA
GGTCCCCGTCCAAAACTTCTACAGTGACTACAACACGACCTACTCCATCC
AGGCCTGTCTTCGCTCCTGCTTCCAAGACCACATGATCCGTAACTGCAAC
TGTGGCCACTACCTGTACCCACTGCCCCGTGGGGAGAAATACTGCAACAA
CCGGGACTTCCCAGACTGGGCCCATTGCTACTCAGATCTACAGATGAGTG
TGGCGCAGAGAGAGACCTGCATTGGCATGTGCAAGGAGTCCTGCAATGAC
ACCCAGTACAAGATGACCATCTCCATGGCTGACTGGCCTTCTGAGGCCTC
CGAGGACTGGATTTTCCACGTCTTGTCTCAGGAGCGGGACCAAAGCACCA
ATATCACCCTGAGCAGGAAGGGAATTGTCAAGCTCAACATCTACTTCCAA
GAATTTAACTATCGCACCATTGAAGAATCAGCAGCCAATAACATCGTCTG
GCTGCTCTCGAATCTGGGTGGCCAGTTTGGCTTCTGGATGGGGGGCTCTG
TGCTGTGCCTCATCGAGTTTGGGGAGATCATCATCGACTTTGTGTGGATC
ACCATCATCAAGCTGGTGGCCCTTGGCCAAGAGCCTACGGCAGCGCTGAG
CCAAGCCAGCTACGCTGGCCCACCGCCCACCGTGGCCGAGCTGGTGGAGG
CCCACACCAACTTTGGCTTCCAGCCTGACACGGCCCCCCGCAGCCCCAAC
ACTGGGCCCTACCCCAGTGAGCAGGCCCTGCCCATCCCAGGCACCCCGCC
CCCCAACTATGACTCCCTGCGTCTGCAGCCGCTGGACGTCATCGAGTCTG
ACAGTGAGGGTGATGCCATCTAA 3) SEQ ID NO: 11: SCNN1B mRNA sequence (Genbank: NM_000336.2, 2597 bp)
GTGCTTCCCCGCCCCTGAACCTGCTCCCTCCCCAGTCGGTCTCGCCGCGCT
CGCCGGGTGTCCCAGTGTCACCAACACTCGGCCGCCGCCGCCAGCTTGGC
GCGCACCGCCGCCTCCGCCACCGCCGACAGCGCGCATCCTCCGTGTCCCC
GCTCCGCCGCCCGAGCAGGTGCCACTATGCACGTGAAGAAGTACCTGCTG
AAGGGCCTGCATCGGCTGCAGAAGGGCCCCGGCTACACGTACAAGGAGCT
GCTGGTGTGGTACTGCGACAACACCAACACCCACGGCCCCAAGCGCATCA
TCTGTGAGGGCCCCAAGAAGAAAGCCATGTGGTTCCTGCTCACCCTGCTC
TTCGCCGCCCTCGTCTGCTGGCAGTGGGGCATCTTCATCAGGACCTACTT
GAGCTGGGAGGTCAGCGTCTCCCTCTCCGTAGGCTTCAAGACCATGGACT
TCCCTGCCGTCACCATCTGCAATGCTAGCCCCTTCAAGTATTCCAAAATC
AAGCATTTGCTGAAGGACCTGGATGAGCTGATGGAAGCTGTCCTGGAGAG
AATCCTGGCTCCTGAGCTAAGCCATGCCAATGCCACCAGGAACCTGAACT
TCTCCATCTGGAACCACACACCCCTGGTCCTTATTGATGAACGGAACCCC
CACCACCCCATGGTCCTTGATCTCTTTGGAGACAACCACAATGGCTTAAC
AAGCAGCTCAGCATCAGAAAAGATCTGTAATGCCCACGGGTGCAAAATGG
CCATGAGACTATGTAGCCTCAACAGGACCCAGTGTACCTTCCGGAACTTC
ACCAGTGCTACCCAGGCATTGACAGAGTGGTACATCCTGCAGGCCACCAA
CATCTTTGCACAGGTGCCACAGCAGGAGCTAGTAGAGATGAGCTACCCCG
GCGAGCAGATGATCCTGGCCTGCCTATTCGGAGCTGAGCCCTGCAACTAC
CGGAACTTCACGTCCATCTTCTACCCTCACTATGGCAACTGTTACATCTT
CAACTGGGGCATGACAGAGAAGGCACTTCCTTCGGCCAACCCTGGAACTG
AATTCGGCCTGAAGTTGATCCTGGACATAGGCCAGGAAGACTACGTCCCC
TTCCTTGCGTCCACGGCCGGGGTCAGGCTGATGCTTCACGAGCAGAGGTC
ATACCCCTTCATCAGAGATGAGGGCATCTACGCCATGTCGGGGACAGAGA
CGTCCATCGGGGTACTCGTGGACAAGCTTCAGCGCATGGGGGAGCCCTAC
AGCCCGTGCACCGTGAATGGTTCTGAGGTCCCCGTCCAAAACTTCTACAG
TGACTACAACACGACCTACTCCATCCAGGCCTGTCTTCGCTCCTGCTTCC
AAGACCACATGATCCGTAACTGCAACTGTGGCCACTACCTGTACCCACTG
CCCCGTGGGGAGAAATACTGCAACAACCGGGACTTCCCAGACTGGGCCCA
TTGCTACTCAGATCTACAGATGAGCGTGGCGCAGAGAGAGACCTGCATTG
GCATGTGCAAGGAGTCCTGCAATGACACCCAGTACAAGATGACCATCTCC
ATGGCTGACTGGCCTTCTGAGGCCTCCGAGGACTGGATTTTCCACGTCTT
GTCTCAGGAGCGGGACCAAAGCACCAATATCACCCTGAGCAGGAAGGGAA
TTGTCAAGCTCAACATCTACTTCCAAGAATTTAACTATCGCACCATTGAA
GAATCAGCAGCCAATAACATCGTCTGGCTGCTCTCGAATCTGGGTGGCCA
GTTTGGCTTCTGGATGGGGGGCTCTGTGCTGTGCCTCATCGAGTTTGGGG
AGATCATCATCGACTTTGTGTGGATCACCATCATCAAGCTGGTGGCCCTT
GGCCAAGAGCCTACGGCAGCGCTGAGCCAAGCCAGCTACGCTGGCCACC
GCCCACCGTGGCCGAGCTGGTGGAGGCCCACACCAACTTTGGCTTCCAGC
CTGACACGGCCCCCCGCAGCCCCAACACTGGGCCCTACCCCAGTGAGCAG
GCCCTGCCCATCCCAGGCACCCCGCCCCCCAACTATGACTCCCTGCGTCT
GCAGCCGCTGGACGTCATCGAGTCTGACAGTGAGGGTGATGCCATCTAAC
CTGCCCCTGCCCACCCCGGGCGGCTGAAACTCACTGAGCAGCCAAGACT
GTTGCCCGAGGCCTCACTGTATGGTGCCCTCTCCAAAGGGTCGGGAGGGT
AGCTCTCCAGGCCAGAGCTTGTGTCCTTCAACAGAGAGGCCAGCGGCAAC
TGGTCCGTTACTGGCCAAGGGCTCTAGAATCACGGTGCTGGTACAGGA
TGCAGGAATAAATTGTATCTTCACCTGGTTCTCTACCCTCGTCCCTACCTG
TCCTGATCCTGGTCCTGAAGACCCCTCGGAACACCCTCTCCTGGTGGCAG
GCCACTTCCCTCCCAGTGCCAGTCTCCATCCACCCCAGGAGGAACAGGC
GGGTGGGCCATGTGGTTTTCTCCTTCCTGGCCTTGGCTGGCCTCTGGGGC
AGGGGTGGTGGAGAGATGGAAGGGCATCAGGTGTAGGGACCCTGCCAAGT
GGCACCTGATTTACTCTAGAAAATAAAAGTAGAAAATACTGAGTCCA 4) SEQ ID NO: 12: SCNN1B protein sequence, 640 amino acids
MHVKKYLLKGLHRLQKGPGYTYKELLVWYCDNTNTHGPKRIICEGPKKKA
MWFLLTLLFAALVCWQWGIFIRTYLSWEVSVSLSVGFKTMDFPAVTICNA
SPFKYSKIKHLLKDLDELMEAVLERILAPELSHANATRNLNFSIWNHTPL
VLIDERNPHHPMVLDLFGDNHNGLTSSSASEKICNAHGCKMAMRLCSLNR
TQCTFRNFTSATQALTEWYILQATNIFAQVPQQELVEMSYPGEQMILACL
FGAEPCNYRNFTSIFYPHYGNCYIFNWGMTEKALPSANPGTEFGLKLILD
IGQEDYVPFLASTAGVRLMLHEQRSYPFIRDEGIYAMSGTETSIGVLVDK
LQRMGEPYSPCTVNGSEVPVQNFYSDYNTTYSIQACLRSCFQDHMIRNCN
CGHYLYPLPRGEKYCNNRDFPDWAHCYSDLQMSVAQRETCIGMCKESCND
TQYKMTISMADWPSEASEDWIFHVLSQERDQSTNITLSRKGIVKLNIYFQ
EFNYRTIEESAANNIVWLLSNLGGQFGFWMGGSVLCLIEFGEIIIDFVWI
TIIKLVALAKSLRQRRAQASYAGPPPTVAELVEAHTNFGFQPDTAPRSPN
TGPYPSEQALPIPGTPPPNYDSLRLQPLDVIESDSEGDAI

TABLE 3

Clinicopathological characteristics and SCNN1B expression status in tumor tissues of gastric cancer patients

| Variable | Univariate Cox regression analysis | | Multivariate Cox regression analysis | |
|---|---|---|---|---|
| | HR (95% CI) | p Value | HR (95% CI) | p Value |
| Age | 1.014 (1.000 to 1.029) | 0.048 | 1.023 (1.007 to 1.039) | 0.004 |
| Gender | | | | |
| Male | 1 | | 1 | |
| Female | 1.208 (0.861 to 1.695) | 0.275 | 1.134 (0.780 to 1.648) | 0.509 |
| Helicobacter pylori infection | | | | |
| Negative | 1 | | | |
| Positive | 0.788 (0.568 to 1.094) | 0.154 | | |
| Lauren | | <0.001 | | |
| Intestinal | 1 | | 1 | |
| Diffuse | 1.700 (1.188 to 2.433) | 0.004 | 1.418 (0.957 to 2.101) | 0.082 |
| Mixed | 2.404 (1.490 to 3.878) | <0.001 | 1.760 (1.072 to 2.889) | 0.025 |
| Differentiation | | 0.024 | | |
| Well | 1 | | 1 | |
| Moderate | 3.322 (0.806 to 13.687) | 0.097 | 3.118 (0.423 to 23.000) | 0.265 |
| Poor | 4.626 (1.138 to 18.813) | 0.032 | 2.676 (0.349 to 20.498) | 0.343 |
| lymphatic metastasis | | | | |
| Negative | 1 | | | |
| Positive | 5.236 (2.949 to 9.297) | <0.001 | | |
| TNM stage | | <0.001 | | |
| Early stage | 1 | | 1 | |
| Late stage | 5.664 (3.566 to 8.996) | <0.001 | 4.360 (2.629 to 7.229) | <0.001 |
| SCNN1B expression in cytoplasm | | <0.001 | | |
| Weak | 1 | | 1 | |
| Moderate | 0.482 (0.320 to 0.726) | <0.001 | 0.547 (0.360 to 0.829) | 0.005 |
| Strong | 0.247 (0.091 to 0.674) | 0.006 | 0.353 (0.128 to 0.971) | 0.044 |

LIST OF REFERENCES

1. Grady W M, Carethers J M. Genomic and epigenetic instability in colorectal cancer pathogenesis. Gastroenterology. 2008; 135:1079-99.
2. Rossier B C, Pradervand S, Schild L, Hummler E. Epithelial sodium channel and the control of sodium balance: interaction between genetic and environmental factors. Annu Rev Physiol. 2002; 64:877-97.
3. Soundararajan R, Melters D, Shih I C, Wang J, Pearce D. Epithelial sodium channel regulated by differential composition of a signaling complex. Proc Natl Acad Sci USA. 2009; 106(19):7804-9. Annu Rev Physiol. 2002; 64:877-97.
4. Dalgin G S, Dreyer M, Williams T, King T, DeLisi C, Liou L S. Identification of novel epigenetic markers for clear cell renal cell carcinoma. J Urol. 2008; 180(3):1126-30.
5. Yu J, Cheng Y Y, Tao Q, et al. Methylation of Protocadherin 10, a Novel Tumor Suppressor, Is Associated With Poor Prognosis in Patients With Gastric Cancer. Gastroenterology. 2009; 136:640-51.

What is claimed is:

1. A method for measuring expression level of SCNN1B protein in a subject, comprising the step of:
   (a) selecting a subject who has an increased risk for gastric cancer; and
   (b) contacting a stomach mucosa sample taken from the subject with an antibody that specifically binds to a SCNN1B protein having the amino acid sequence of SEQ ID NO:12, thereby determining the expression level of SCNN1B protein in the stomach mucosa sample.

2. The method of claim 1, further comprising obtaining the stomach mucosa sample from the subject prior to step (b).

3. The method of claim 1, wherein the subject has a family history of gastric cancer.

4. The method of claim 3, wherein the subject is asymptomatic of gastric cancer.

5. The method of claim 3, wherein the subject has symptoms of gastric cancer.

6. The method of claim 1, further comprising repeating step (b) at a later time using a second sample of the sample type taken from the subject at the later time.

7. The method of claim 1, wherein the subject has environmental risk factors for gastric cancer.

8. A method for measuring expression level of SCNN1B protein in a subject, comprising the step of:
   (a) obtaining a stomach mucosa sample from a subject who has an increased risk for gastric cancer; and
   (b) contacting the stomach mucosa sample with an antibody that specifically binds to a SCNN1B protein having the amino acid sequence of SEQ ID NO:12, thereby determining the expression level of SCNN1B protein in the stomach mucosa sample.

9. The method of claim 8, wherein the subject has a family history of gastric cancer.

10. The method of claim 8, wherein the subject has environmental risk factors for gastric cancer.

11. The method of claim 9, wherein the subject is asymptomatic of gastric cancer.

12. The method of claim 9, wherein the subject has symptoms of gastric cancer.

13. The method of claim 8, further comprising repeating step (b) at a later time using a second sample of the sample type taken from the subject at the later time.

* * * * *